United States Patent
Reddy et al.

(10) Patent No.: US 11,464,990 B2
(45) Date of Patent: Oct. 11, 2022

(54) AZYGOS, INTERNAL THORACIC, AND/OR INTERCOSTAL VEIN IMPLANTATION AND USE OF MEDICAL DEVICES

(71) Applicant: CARDIAC PACEMAKERS, INC., St. Paul, MN (US)

(72) Inventors: G. Shantanu Reddy, Minneapolis, MN (US); Eric Falbe Hammill, Ham Lake, MN (US); James O. Gilkerson, Stillwater, MN (US); Ramesh Wariar, Blaine, MN (US); Pramodsingh Hirasingh Thakur, Woodbury, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 186 days.

(21) Appl. No.: 16/930,730

(22) Filed: Jul. 16, 2020

(65) Prior Publication Data

US 2020/0346023 A1 Nov. 5, 2020

Related U.S. Application Data

(63) Continuation of application No. 15/847,490, filed on Dec. 19, 2017, now Pat. No. 10,751,543.

(Continued)

(51) Int. Cl.
*A61N 1/378* (2006.01)
*A61N 1/375* (2006.01)
(Continued)

(52) U.S. Cl.
CPC ....... *A61N 1/3787* (2013.01); *A61N 1/37512* (2017.08); *A61N 1/3962* (2013.01);
(Continued)

(58) Field of Classification Search
CPC ...... A61N 1/056; A61N 1/0563; A61N 1/362; A61N 1/3956; A61N 1/05; A61N 1/368;
(Continued)

(56) References Cited

U.S. PATENT DOCUMENTS

| 5,331,966 A | 7/1994 | Bennett et al. |
| 6,647,292 B1 | 11/2003 | Bardy et al. |

(Continued)

FOREIGN PATENT DOCUMENTS

| WO | 2016148928 A1 | 9/2016 |
| WO | 2016149262 A1 | 9/2016 |

OTHER PUBLICATIONS

Moeinipour et al., "A Rare Central Venous Catheter Malposition: A Case Report," Anesth Pain Med., 4(1): 1-3, Feb. 5, 2014.

(Continued)

*Primary Examiner* — Deborah L Malamud
(74) *Attorney, Agent, or Firm* — Seager, Tufte & Wickhem LLP

(57) ABSTRACT

Cardiac therapy devices in the form of pacemakers and/or defibrillators including one or more leads with electrodes implanted in a vein in a posterior position in combination with one or more leads with electrodes implanted in an anterior position. The posterior position may be chosen from one or more of the azygos, hemiazygos, accessory hemiazygos, or posterior intercostal veins. The anterior position may be chosen from the internal thoracic vein, an anterior intercostal vein, or an anterior subcutaneous location. In other examples, sensors are placed for use by a cardiac monitoring or therapy system in one or more of the internal thoracic vein, the azygos vein, the hemiazygos vein, the accessory hemiazygos vein, and/or an anterior or posterior intercostal vein.

12 Claims, 27 Drawing Sheets

Related U.S. Application Data

(60) Provisional application No. 62/437,693, filed on Dec. 22, 2016.

(51) Int. Cl.
    *A61N 1/39*         (2006.01)
    *A61N 1/372*       (2006.01)
    *A61N 1/05*         (2006.01)

(52) U.S. Cl.
    CPC .......... *A61N 1/0563* (2013.01); *A61N 1/3756* (2013.01); *A61N 1/37211* (2013.01); *A61N 1/37288* (2013.01)

(58) Field of Classification Search
CPC ................. A61N 1/39; A61N 1/39622; A61N 2001/0585; A61N 1/0587; A61N 1/3622; A61N 1/37516; A61N 1/00; A61N 1/306; A61N 1/37; A61B 5/0031; A61B 5/6876; A61B 5/4836
See application file for complete search history.

(56) References Cited

U.S. PATENT DOCUMENTS

| | | |
|---|---|---|
| 6,721,597 B1 | 4/2004 | Bardy et al. |
| 7,149,575 B2 | 12/2006 | Ostroff et al. |
| 7,655,014 B2 | 2/2010 | Ko et al. |
| 7,783,340 B2 | 8/2010 | Sanghera et al. |
| 7,818,068 B2 | 10/2010 | Meadows et al. |
| 7,969,922 B2 | 6/2011 | He et al. |
| 8,005,543 B2 | 8/2011 | Libbus et al. |
| 8,157,313 B2 | 4/2012 | Ko et al. |
| 8,386,048 B2 | 2/2013 | McClure et al. |
| 8,483,843 B2 | 7/2013 | Sanghera et al. |
| 8,543,216 B2 | 9/2013 | Carbunaru et al. |
| 10,751,543 B2 * | 8/2020 | Reddy ................. A61N 1/3962 |
| 2005/0043765 A1 | 2/2005 | Williams et al. |
| 2012/0029335 A1 | 2/2012 | Sudam et al. |
| 2015/0025612 A1 | 1/2015 | Haasl et al. |
| 2015/0051610 A1 | 2/2015 | Schmidt et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0224320 A1 | 8/2015 | Stahmann |
| 2015/0297902 A1 | 10/2015 | Stahmann et al. |
| 2015/0352358 A1 | 12/2015 | Atwater |
| 2015/0360036 A1 | 12/2015 | Kane et al. |
| 2016/0038742 A1 | 2/2016 | Stahmann et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0228712 A1 | 8/2016 | Koop |
| 2016/0256692 A1 | 9/2016 | Baru |
| 2017/0021159 A1 | 1/2017 | Reddy et al. |
| 2018/0036527 A1 | 2/2018 | Reddy et al. |
| 2018/0036547 A1 | 2/2018 | Reddy |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0178018 A1 | 6/2018 | Reddy et al. |
| 2018/0178019 A1 | 6/2018 | Reddy et al. |
| 2018/0193060 A1 | 7/2018 | Reddy et al. |
| 2018/0214686 A1 | 8/2018 | De Kock et al. |
| 2018/0256890 A1 | 9/2018 | Fuhs et al. |
| 2018/0264270 A1 | 9/2018 | Koop et al. |
| 2018/0296824 A1 | 10/2018 | De Kocke et al. |
| 2018/0325480 A1 | 11/2018 | Liu et al. |
| 2018/0344200 A1 | 12/2018 | Thakur et al. |
| 2018/0344252 A1 | 12/2018 | An et al. |

OTHER PUBLICATIONS

Schuder et al., "Experimental Ventricular Defibrillation with an Automatic and Completely Implanted System," Trans. Amer. Soc. Artif. Int. Organs, XVI: 207-212, 1970.

Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.

Ghosh et al., "A Rare Malposition of the Thoracic Venous Catheter Introduced via the Left Internal Jugular Vein," Indian J. Crit. Care Med., 12(4): 201-203, Oct.-Dec. 2008.

Loukas et al.,"The Clinical Anatomy of the Internal Thoracic Veins," Folia Morphol, 66(1): 25-32, 2007.

Advisory Action Before the Filing of an Appeal Brief for U.S. Appl. No. 15/667,167, dated Mar. 21, 2019.

Final Office Action for U.S. Appl. No. 15/667,167, dated Jan. 10, 2019.

Non-Final Office Action for U.S. Appl. No. 15/667,167, dated Jun. 26, 2018.

Non-Final Office Action for U.S. Appl. No. 15/667,167, dated Aug. 7, 2019.

Final Office Action for U.S. Appl. No. 15/667,221, dated Apr. 11, 2019.

Non-Final Office Action for U.S. Appl. No. 15/667,221, dated Oct. 1, 2018.

Notice of Allowance and Fees Due for U.S. Appl. No. 15/667,221, dated Jul. 11, 2019.

Amendment for U.S. Appl. No. 15/667,167, dated Sep. 17, 2018.
Amendment for U.S. Appl. No. 15/667,167, dated Oct. 9, 2019.
Amendment After Final Office Action for U.S. Appl. No. 15/667,167, dated Mar. 11, 2019.
Request for Continued Examination (RCE) for U.S. Appl. No. 15/667,167, dated Apr. 10, 2019.
Amendment for U.S. Appl. No. 15/667,221, dated Dec. 21, 2018.
Amendment After Final Office Action for U.S. Appl. No. 15/667,221, dated May 22, 2019.

* cited by examiner

AZYGOS, INTERNAL THORACIC, AND/OR INTERCOSTAL VEIN IMPLANTATION AND USE OF MEDICAL DEVICES

CROSS REFERENCE TO RELATED APPLICATIONS

The present application is a continuation of U.S. patent application Ser. No. 15/847,490, filed on Dec. 19, 2017, and titled AZYGOS, INTERNAL THORACIC, AND/OR INTERCOSTAL VEIN IMPLANTATION AND USE OF MEDICAL DEVICES, which claims the benefit of and priority to U.S. Provisional Patent Application Ser. No. 62/437,693, filed Dec. 22, 2016, and titled AZYGOS, INTERNAL THORACIC, AND/OR INTERCOSTAL VEIN IMPLANTATION AND USE OF MEDICAL DEVICES, the disclosures of which are incorporated herein by reference.

BACKGROUND

Implantable pacemakers, defibrillators, cardiac monitors, and other therapy or sensing apparatuses are known for implantation within the heart, on the heart, and subcutaneously over the ribcage. Devices placed within the heart, or having leads attached to or extending into the heart have advantages such as, for example, lower energy necessary for therapy. Devices placed subcutaneously over the ribcage require higher energy, however they limit serious injury associated with removal of chronically implanted devices. Additional and alternative implantation locations and devices for such use are desired.

Overview

The present inventors have recognized, among other things, that a problem to be solved is the need for additional alternatives to existing implant techniques and locations for therapy and sensing apparatuses in the thorax of a patient.

A first illustrative and non-limiting example takes the form of an implantable device system comprising a plurality of leads and electrodes for therapy delivery purposes, the system comprising: a first lead having a first electrode for therapy delivery purposes, the first lead adapted to place the first electrode in an internal thoracic vein; a second lead having a second electrode for therapy delivery purposes, the second lead adapted to place the second electrode in a selected one of the azygos, hemiazygos, or accessory hemiazygos veins; and an implantable canister housing operational circuitry configured to provide therapeutic electrical stimulus via the first and second electrodes when said first electrode is disposed in the internal thoracic vein and said second electrode is disposed in the selected one of the azygos, hemiazygos, or accessory hemiazygos veins.

Additionally or alternatively to the first illustrative and non-limiting example, the therapeutic electrical stimulus may have an energy in the range of about 20 to about 60 Joules, though lower and higher ranges may be used instead.

Additionally or alternatively to the first illustrative and non-limiting example, and variants thereof, the implantable canister and first and second leads are adapted to facilitate placement of the canister in a location near the clavicle such that the first and second leads enter and pass through at least a portion of a brachiocephalic vein.

Additionally or alternatively to the first illustrative and non-limiting example, and variants thereof, the implantable canister and first and second leads are adapted to facilitate placement of the canister in the left axilla such that the first and second leads enter and pass through one or more intercostal veins.

Additionally or alternatively to the first illustrative and non-limiting example, and variants thereof, the first lead comprises a third therapy delivery electrode, and the operational circuitry is configured to shape therapy delivery to target a desired portion of the heart using the first, second and third electrodes.

Additionally or alternatively to the first illustrative and non-limiting example, and variants thereof, the second lead comprise a third therapy delivery electrode, and the operational circuitry is configured to shape therapy delivery to target a desired portion of the heart using the first, second and third electrodes.

Additionally or alternatively to the first illustrative and non-limiting example, and variants thereof, at least one of the first or second leads further comprises a sensor for sensing a patient condition.

Additionally or alternatively to the first illustrative and non-limiting example, and variants thereof, the system may further comprise a sensor adapted for placement in an internal thoracic vein of the patient, the sensor being adapted for such placement without the use of a lead, wherein the sensor is configured to communicate with the operational circuitry in the implantable canister.

Additionally or alternatively to the first illustrative and non-limiting example, and variants thereof, the system may further comprise a sensor adapted for placement in a selected one of the azygos, accessory hemiazygos, or hemiazygos veins of the patient, the sensor being adapted for such placement without the use of a lead, wherein the sensor is configured to communicate with the operational circuitry in the implantable canister.

Additionally or alternatively to the first illustrative and non-limiting example, and variants thereof, the system may further comprise a sensor adapted for placement in an intercostal vein of the patient, the sensor being adapted for such placement without the use of a lead, wherein the sensor is configured to communicate with the operational circuitry in the implantable canister.

Additionally or alternatively, the sensor may be an optical sensor, an accelerometer, a temperature sensor, a sensor adapted to sense heart sounds, a sensor adapted to sense cardiac electrical signals, a sensor adapted to sense pressure waves, and/or a sensor adapted to sense impedance.

A second illustrative and non-limiting example takes the form of a method of treating a patient comprising: implanting a first electrode in the patient in at least one of the internal thoracic veins; implanting a second electrode in the patient in at least one of the azygos, hemiazygos, or accessory hemiazygos veins; and coupling the first electrode and second electrode to operational circuitry of an implantable cardiac monitoring or stimulus system.

Additionally or alternatively to the second illustrative and non-limiting example, and variants thereof, the steps of implanting the first electrode and implanting the second electrode are both performed by passing through the brachiocephalic vein.

Additionally or alternatively to the second illustrative and non-limiting example, and variants thereof, the step of implanting the first electrode does not include passing through the brachiocephalic vein, and the step of implanting the second electrode does include passing through the brachiocephalic vein through the azygos ostium.

Additionally or alternatively to the second illustrative and non-limiting example, and variants thereof, the step of implanting the first electrode comprises directly accessing the internal thoracic vein at a parasternal location between two ribs.

Additionally or alternatively to the second illustrative and non-limiting example, and variants thereof, the step of implanting the first electrode comprises accessing a superior epigastric vein of the patient at a location inferior to the rib margin and then accessing the internal thoracic vein via the superior epigastric vein.

Additionally or alternatively to the second illustrative and non-limiting example, and variants thereof, the step of implanting the first electrode comprises accessing an intercostal vein and then accessing the internal thoracic vein from the intercostal vein.

Additionally or alternatively to the second illustrative and non-limiting example, and variants thereof, the steps of implanting the first electrode and implanting the second electrode are both performed by passing through an intercostal vein from an axillary position, with the first electrode being implanted by passing through an anterior portion of the intercostal vein from the axillary position, and the second electrode being implanted by passing through a posterior portion of the intercostal vein from the axillary position.

Additionally or alternatively to the second illustrative and non-limiting example, and variants thereof, the first and second electrodes are disposed on respective first and second leads.

Additionally or alternatively to the second illustrative and non-limiting example, and variants thereof, the method may further comprise anchoring at least one of the first and second leads in a vein.

A third illustrative and non-limiting example takes the form of a method of treating a patient comprising delivering cardiac electrical therapy between: a first electrode disposed in an internal thoracic vein; and a second electrode disposed in at least one of the azygos, hemiazygos, or accessory hemiazygos veins.

Additionally or alternatively to the third illustrative and non-limiting example, and variants thereof, the cardiac electrical therapy is a pacing output.

Additionally or alternatively to the third illustrative and non-limiting example, and variants thereof, the first electrode is disposed in the right internal thoracic vein and the second electrode is disposed in the azygos vein to direct the pacing output to the right ventricle of the patient.

Additionally or alternatively to the third illustrative and non-limiting example, and variants thereof, the first electrode is disposed in the left internal thoracic vein and the second electrode is disposed in the hemiazygos vein to direct the pacing output to the left ventricle of the patient.

Additionally or alternatively to the third illustrative and non-limiting example, and variants thereof, the first electrode is disposed in the left internal thoracic vein and the second electrode is disposed in the accessory hemiazygos vein to direct the pacing output to the left ventricle of the patient.

Additionally or alternatively to the third illustrative and non-limiting example, and variants thereof, the cardiac electrical therapy is a defibrillation output.

Additionally or alternatively to the third illustrative and non-limiting example, and variants thereof, the first electrode is disposed in the left internal thoracic vein and the second electrode is disposed in the azygos vein to direct the defibrillation output across the heart.

Additionally or alternatively to the third illustrative and non-limiting example, and variants thereof, the first electrode is disposed in the right internal thoracic vein and the second electrode is disposed in the hemiazygos vein to direct the defibrillation output across the heart.

Additionally or alternatively to the third illustrative and non-limiting example, and variants thereof, the first electrode is disposed in the right internal thoracic vein and the second electrode is dispose in the accessory hemiazygos vein to direct the defibrillation output across the heart.

Additionally or alternatively to the third illustrative and non-limiting example, and variants thereof, the method may further comprise using a third electrode electrically common to the first electrode to steer the defibrillation therapy, wherein the third electrode is disposed in one of an internal thoracic vein or an intercostal vein.

Additionally or alternatively to the third illustrative and non-limiting example, and variants thereof, the method may further comprise using a third electrode electrically common to the second electrode to steer the defibrillation therapy, wherein the third electrode is disposed in one the azygos vein, the hemiazygos vein, the accessory hemiazygos vein, or an intercostal vein.

A fourth illustrative and non-limiting example takes the form of a method of treating a patient comprising implanting a sensor in the azygos vein of the patient.

A fifth illustrative and non-limiting example takes the form of a method of treating a patient comprising implanting a sensor in the hemiazygos vein of the patient.

A sixth illustrative and non-limiting example takes the form of a method of treating a patient comprising implanting a sensor in the accessory hemiazygos vein of the patient.

Additionally or alternatively to the fourth to sixth illustrative, non-limiting examples, and variants thereof, the step of implanting comprises passing an implanting catheter via the brachiocephalic vein into the azygos vein, and advancing therefrom to a target implant location for the sensor.

Additionally or alternatively to the fourth to sixth illustrative, non-limiting examples, and variants thereof, the step of implanting comprises inserting a delivery catheter into an intercostal vein of the patient and passing therethrough to a target implant location for the sensor.

Additionally or alternatively to the fourth to sixth illustrative, non-limiting examples, and variants thereof, the step of inserting a delivery catheter into the intercostal vein is performed by first accessing an internal thoracic vein of the patient and passing thereform into the intercostal vein.

Additionally or alternatively to the fourth to sixth illustrative, non-limiting examples, and variants thereof, the step of inserting a delivery catheter into the intercostal vein is performed by inserting a needle and at least one of a guidewire and an introducer into the intercostal vein.

Additionally or alternatively to the fourth to sixth illustrative, non-limiting examples, and variants thereof, wherein the step of inserting a needle into the intercostal vein is performed using ultrasound guidance.

A seventh illustrative and non-limiting example takes the form of a method of treating a patient comprising implanting a sensor in an intercostal vein of the patient.

Additionally or alternatively to the seventh illustrative, non-limiting example, and variants thereof, the step of implanting a sensor comprises inserting a delivery catheter into the azygos vein from the brachiocephalic vein, and advancing the delivery catheter from the azygos vein into the intercostal vein.

Additionally or alternatively to the seventh illustrative, non-limiting example, and variants thereof, the step of implanting a sensor comprises inserting a delivery catheter into the azygos vein from the brachiocephalic vein, then into one of the hemiazygos vein or the accessory hemiazygos vein, and then into the intercostal vein.

Additionally or alternatively to the seventh illustrative, non-limiting example, and variants thereof, the step of implanting a sensor comprises inserting a delivery catheter into an internal thoracic vein from the brachiocephalic vein and then advancing the delivery catheter into the intercostal vein.

Additionally or alternatively to the seventh illustrative, non-limiting example, and variants thereof, the step of implanting a sensor comprises inserting a delivery catheter into an internal thoracic vein at a parasternal location between two ribs of the patient and then advancing the delivery catheter into the intercostal vein.

Additionally or alternatively to the seventh illustrative, non-limiting example, and variants thereof, the step of implanting a sensor comprises inserting a delivery catheter into a superior epigastric vein, then advancing the delivery catheter into an internal thoracic vein, and then advancing the delivery catheter into the intercostal vein.

Additionally or alternatively to the seventh illustrative, non-limiting example, and variants thereof, wherein the step of implanting a sensor comprises inserting a delivery catheter into the intercostal vein percutaneously using a needle and at least one of a guidewire or an introducer sheath.

Additionally or alternatively to the seventh illustrative, non-limiting example, and variants thereof, the step of implanting a sensor comprises inserting the sensor through a needle into the intercostal vein.

An eighth illustrative and non-limiting example takes the form of a method of treating a patient comprising implanting a sensor in an internal thoracic vein of the patient. Such implantation may be performed, for example, by accessing the internal thoracic vein directly at a parasternal location, from an inferior location in the superior epigastric vein, from a superior location in or superior to the brachiocephalic vein(s), or by advancing into the internal thoracic vein from an intercostal vein.

A ninth illustrative and non-limiting example takes the form of a method of treating a patient comprising implanting a sensor in the mediastinum of the patient.

Additionally or alternatively to the ninth illustrative, non-limiting example, and variants thereof, the method further comprises anchoring the sensor to connective tissue in the region of the sternal angle.

Additionally or alternatively to the ninth illustrative, non-limiting example, and variants thereof, the method further comprises anchoring the sensor to connective tissue in the region of the $2^{nd}$ or $3^{rd}$ rib.

Additionally or alternatively to the ninth illustrative, non-limiting example, and variants thereof, the method further comprises anchoring the sensor to connective tissue superior to the ventricles, and/or inferior to or at the manubrium.

Additionally or alternatively to the ninth illustrative, non-limiting example, and variants thereof, the method further comprises anchoring the sensor to connective tissue approximately level with one of the thymus or the aortic arch.

Additionally or alternatively to any of the fourth to ninth illustrative, non-limiting examples, and variants thereof, the sensor may be an optical sensor, a heart sounds sensor, an accelerometer to detect motion, an ultrasound sensor, a temperature sensor, a pressure sensor, a sensor configured to detect an electrical signal.

Additionally or alternatively to any of the fourth to ninth illustrative, non-limiting examples, and variants thereof, the methods may further comprise implanting a plurality of sensors configured to detect and electrical signal, further comprising obtaining signals from the plurality of sensors to calculate an impedance. The electrical signal may be a cardiac signal.

Additionally or alternatively to any of the fourth to ninth illustrative, non-limiting examples, the sensor may comprise communication circuitry to convey data related to the cardiac electrical signal.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
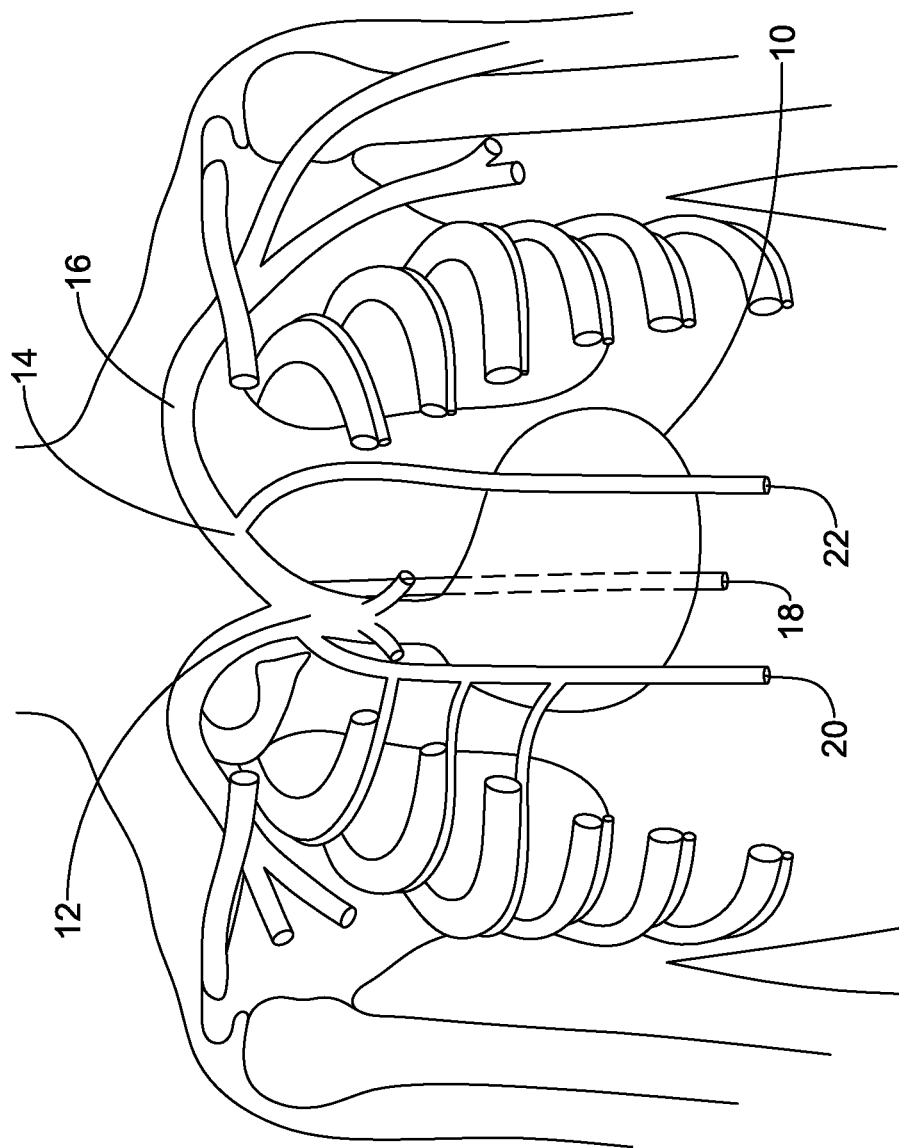
FIG. 1 highlights the venous and other anatomy of the human upper thorax.

FIG. 1 illustrates the thoracic anatomy including location of the internal thoracic veins (ITVs). An outline of the heart is shown at 10, with the superior vena cava (SVC) shown at 12. The brachiocephalic veins 14 couple to the SVC and extend past various cephalic branches to the subclavian vein 16. The azygos vein is shown at 18. The right ITV is shown at 20, and the left ITV is shown at 22.

Certain literature in the field of implantable pacemakers or defibrillators has noted the possibility of the using the azygos vein 18 to implant a lead and electrode to stimulate the vagus nerve (see, for example, U.S. Pat. No. 8,005,543, the disclosure of which is incorporated herein by reference), or as an adjunct to defibrillator function (see Cesario et al., "Azygos vein lead implantation: a novel adjunctive technique for implantable cardioverter defibrillator placement,"

J. Cardiovasc. Electrophysiol., 2004, 15:780-783). However, such proposals have not found widespread acceptance.

U.S. patent application Ser. No. 15/667,167, titled IMPLANTATION OF AN ACTIVE MEDICAL DEVICE USING THE INTERNAL THORACIC VASCULATURE, Ser. No. 15/667,221, titled PACEMAKERS FOR IMPLANT IN THE INTERNAL THORACIC VASCULATURE WITH COMMUNICATION TO OTHER IMPLANTABLE DEVICES, and Ser. No. 15/801,719, titled PARASTERNAL PLACEMENT OF AN ACTIVE MEDICAL DEVICE USING THE INTERNAL THORACIC VASCULATURE, have proposed the use of the internal thoracic veins 20, 22 for placement of one or more leads for an implantable cardiac therapy or monitoring system; such applications are disclosed herein by reference. For example, a subcutaneous implantable defibrillator (such as the Emblem S-ICD System™ from Boston Scientific) may be modified to use the right ITV or left ITV 22 rather than, or in addition to, a parasternal lead position. Such a modification or addition may lower defibrillation and/or pacing thresholds to, for example, reduce power needs and device size, or to facilitate the delivery of chronic bradycardia therapy, pain-free anti-tachycardia pacing (ATP), or cardiac resynchronization therapy (CRT), and/or to provide additional sensing capability.

The ITV may also be thought of as an alternative implantation location to the proposed substernal position discussed in US PG Patent Application Pub. No. 20170021159, titled SUBSTERNAL PLACEMENT OF A PACING OR DEFIBRILLATING ELECTRODE, the disclosure of which is incorporated herein by reference. The ITV may also be used as an access route to a substernal or mediastinal implantation as discussed in U.S. patent application Ser. No. 15/814,990, titled TRANSVENOUS MEDIASTINUM ACCESS FOR THE PLACEMENT OF CARDIAC PACING AND DEFIBRILLATION ELECTRODES, and Ser. No. 15/815,051, titled ELECTRODE FOR SENSING, PACING, AND DEFIBRILLATION DEPLOYABLE IN THE MEDIASTINAL SPACE, the disclosures of which are incorporated herein by reference.

In some examples, implantation in an ITV 20, 22 may be achieved using access via the brachiocephalic vein 14 by advancing from the subclavian vein 16, for example. In other examples, implantation may be by way of the superior epigastric vein, to which each of the ITV 20, 22 connect inferior to the lower rib margin. Implantation may also be by way of a direct access at a parasternal location between two ribs into the ITV using, for example, an ultrasound needle or cut-down technique. Access to the ITV may also be by way of an intercostal vein, which can be accessed using a cut down or ultrasound needle, or other approach, with a lead advanced therefrom to the ITV, as shown in US Provisional Patent Application 62/437,063, titled IMPLANTATION OF AN ACTIVE MEDICAL DEVICE USING THE INTERCOSTAL VEIN.

The musculophrenic vein (not shown) runs along the lower rib margin and may instead, or also, be accessed in a manner that will be termed, for purposes herein, as an inferior access location as it would be inferior to the lowest rib. The musculophrenic vein and superior epigastric vein come together at the lowest end of the ITV. The musculophrenic vein may be accessed using similar methods as for the superior epigastric vein such as by ultrasound-guided Seldinger technique. Due to its adjacency to a bony structure (the lower rib margin), the musculophrenic vein may be useful as its access may be simpler than that of the superior epigastric vein, as the position can be readily ascertained.

Further details on use of the musculophrenic vein for ITV access can be found in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference. Thus, for any example herein referring to the superior epigastric vein, the musculophrenic vein may be used instead for gaining access to the venous system and entering an ITV therefrom.

As further described in several embodiments below, the present inventors propose a further modification by placing one or more cardiac therapy or sensing electrodes in an ITV (or an anterior or lateral position in an intercostal vein) in addition to a posterior position in the azygos vein 18 or in the hemiazygos vein (not shown) and/or accessory hemiazygos vein (not shown), or a posterior position in an intercostal vein.

Figure 2:
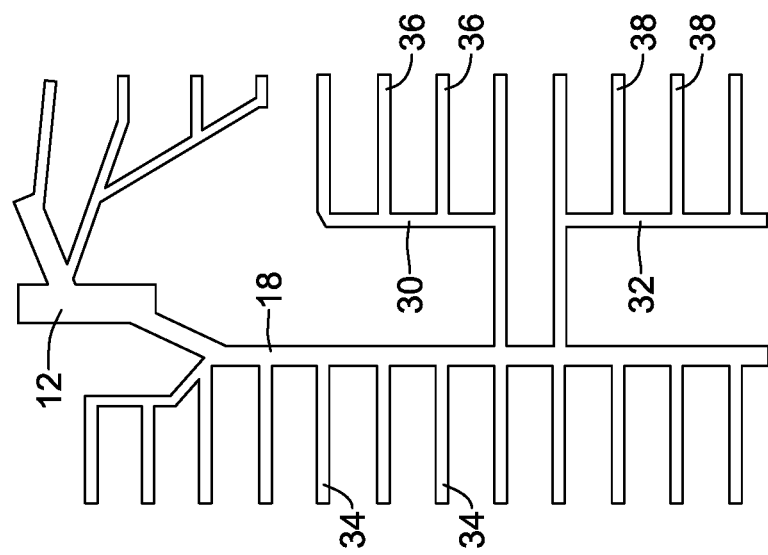
FIG. 2 shows in isolation anterior and posterior venous artery associated with the ribcage.
Figure 2:
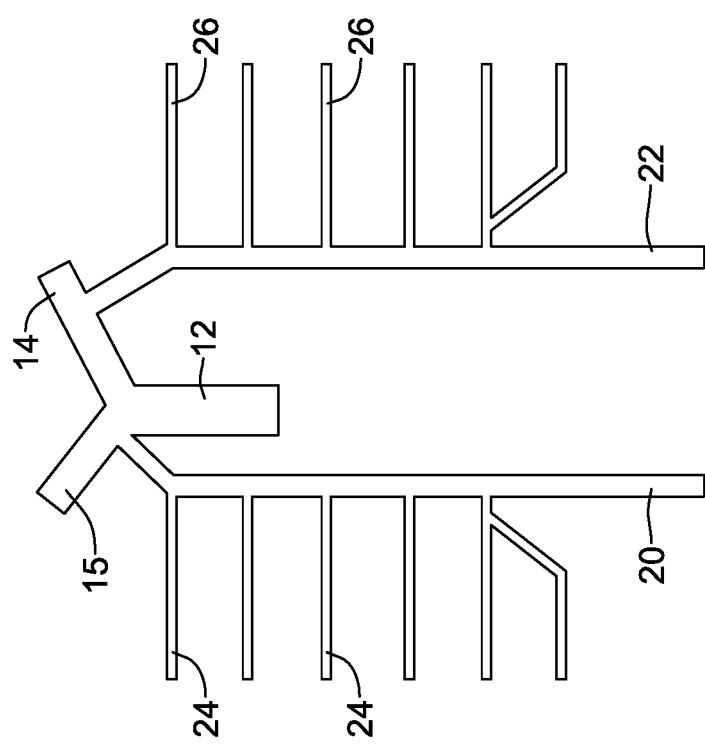

FIG. 2 shows in isolation anterior and posterior veins associated with the ribcage. The left side of the figure shows the anterior vessels. The left brachiocephalic vein is shown at 14, and the right brachiocephalic vein is shown at 15. The right ITV 20 has an ostium to the right brachiocephalic vein 15 and travels inferiorly beneath the ribs, with the several right-sided anterior intercostal veins 24 extending laterally therefrom. The left ITV 22 has an ostium to the left brachiocephalic vein 14 and travels inferiorly beneath the ribs, with the several left sided anterior intercostal veins 26 extending laterally therefrom.

In the posterior mediastinum, the azygos vein 18 connects to the SVC 12 and extends to the back, adjacent the right side of the spine, descending therealong. Several tributary vessels branch out laterally from the azygos vein as the right sided posterior intercostal veins 34. The accessory hemiazygos vein 30 arches off from the azygos vein 18 to the left of midline at about T7-T8, and turns to ascend therefrom along the left side of the spine. Several tributary vessels extend laterally from the accessory hemiazygos vein 30 as the more superior, posterior left sided intercostal veins 36. The hemiazygos vein 32 likewise arches off from the azygos vein 18 to cross the midline and descends therefrom along the left side of the spine. The more inferior posterior left sided intercostal veins 38 arch off from the hemiazygos vein 32. The hemiazygos vein 32 connects as well to the left lumbar vein (not called out in the drawing), analogous to the azygos vein which connects inferiorly to the right lumbar vein.

Each of the anterior intercostal veins 24, 26 travels on the inferior margin of a rib and extends around the thorax to meet one of the posterior intercostal veins 34, 36; separate reference numbers are used for convenience in the figure, but it should be understood that the "anterior" and "posterior" intercostal veins connect. Not all of the branches and veins are shown in FIG. 2. It is conceived that any of the vessels shown may be useful for implantation of a lead or sensor as described below. Several specific examples are shown below.

Figure 3:
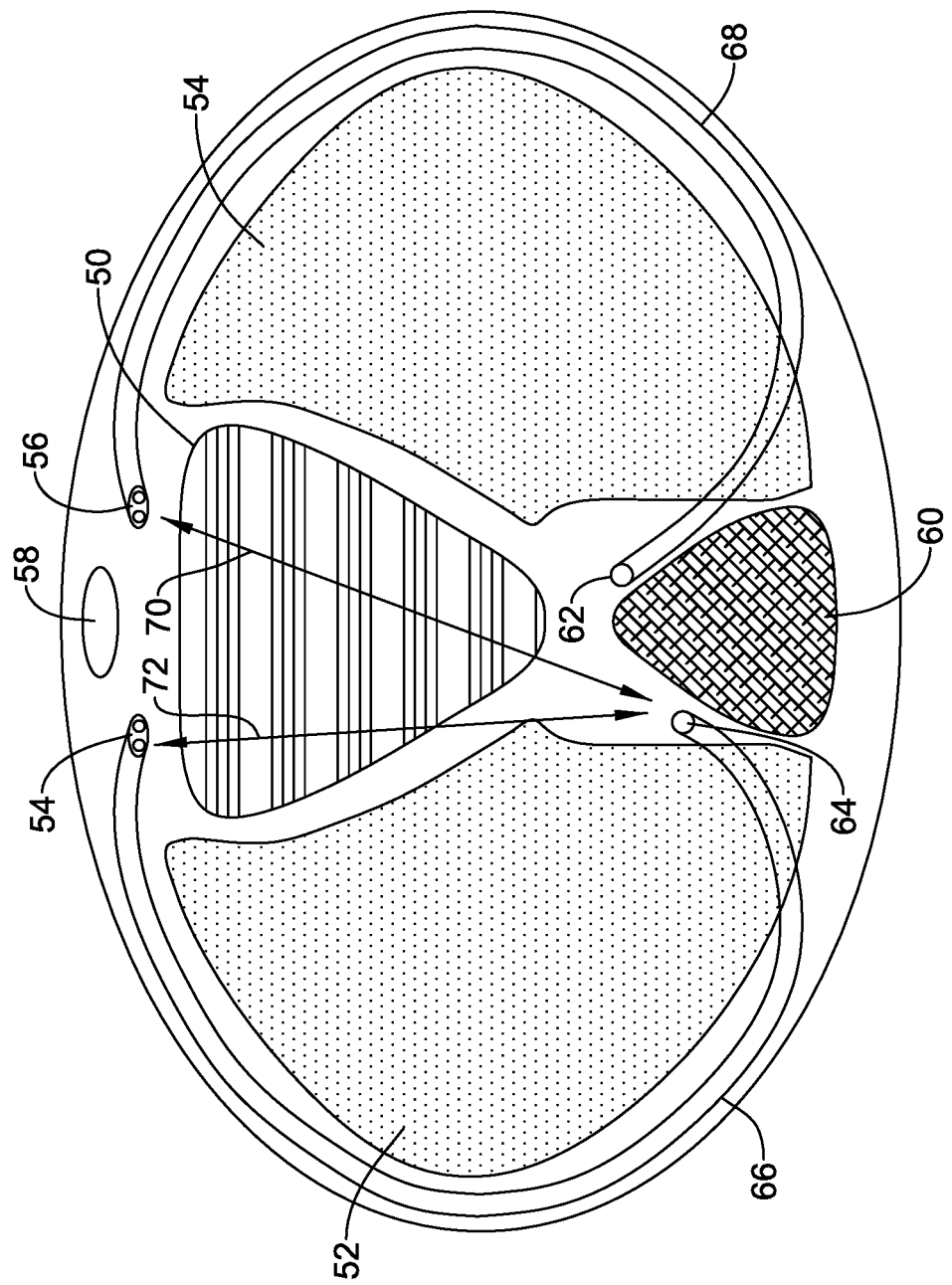
FIG. 3 shows a sectional view of a thorax with certain therapy electrode locations highlighted.

FIG. 3 shows a sectional view of a thorax with certain therapy electrode locations highlighted. The heart is shown illustratively at 50 in a very medial position, with the lungs at 52, 54. Therapy vectors which avoid passing through the lungs 52, 54 may be preferred as lung tissue—and air in particular, is generally of higher impedance than muscle and fat tissue.

The left ITV is shown at 54, and the right ITV at 56, on either side of the sternum 58. The azygos vein is shown at 62 and, depending on the superior/inferior position selected, the vein at 64 may be either the hemiazygos vein (anatomically more inferior) or the accessory hemiazygos vein (anatomically more superior), with these posterior veins on either side of the spinal column 60. As can be seen, a left side intercostal vein 66 connects the left ITV 54 and vein 64, while a right side intercostal vein 68 connects the right ITV 56 to the azygos vein 62. It should be noted that such connections may not occur on a single transverse plane as shown in FIG. 3; the Figure is intended to be schematic in nature and exact anatomical accuracy is not the aim.

The present inventors have recognized that a vector 70 from a right ITV 56 to the vein 64 (whether hemiazygos vein or accessory hemiazygos vein) may be useful to enable pacing or defibrillation therapy focused on the heart. Bone and lung may be avoided using a therapy vector at about the level of T8 to T10. More superior or inferior positions may be used, if desired.

For some patients, the heart 50 may reside somewhat more on the left side, and thus a vector from the azygos vein 62 to the left ITV 54 may be preferred in some examples, rather than that shown. In still other examples, a shock vector 72 may be from the vein 64 (whether hemiazygos vein or accessory hemiazygos vein) to the left ITV 54, to accommodate a more left sided position may be used instead. Such a vector may be achieved in various ways as set forth below.

Figure 4:
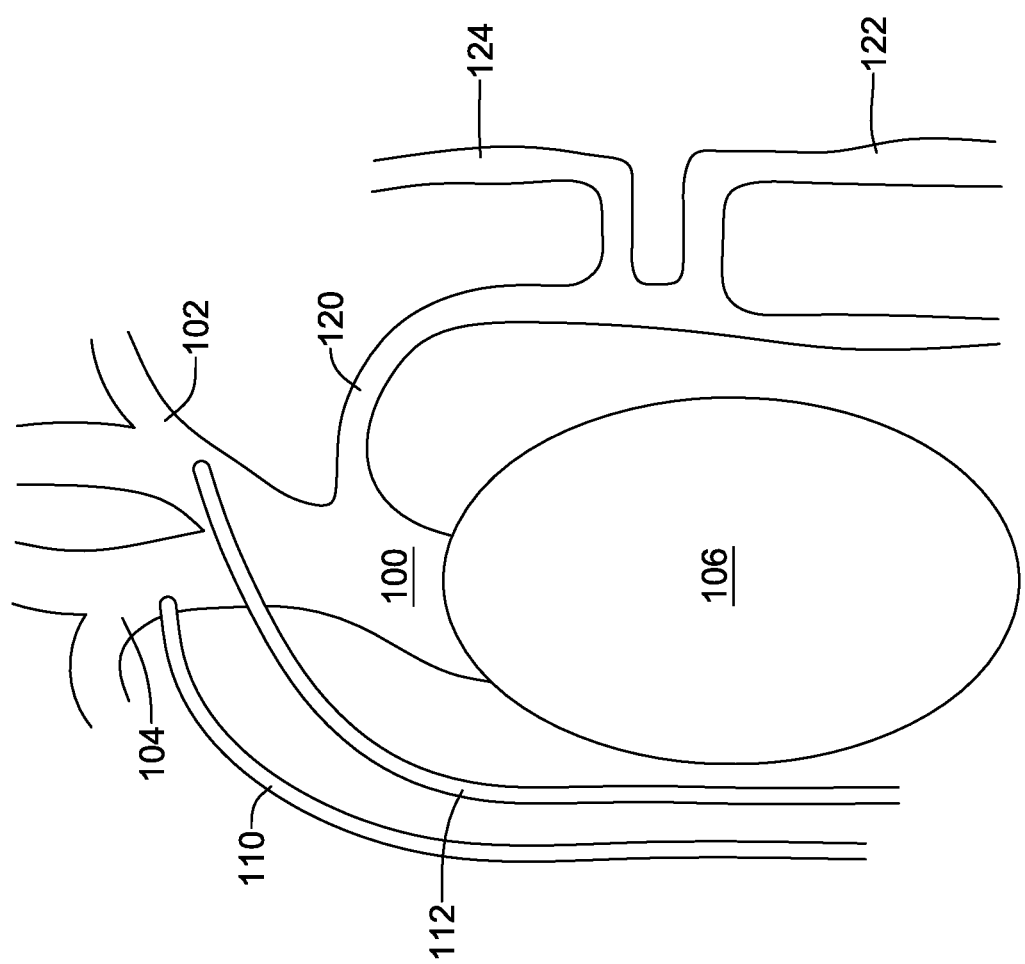
FIG. 4 is a shows venous anatomy and the heart in schematic form.

FIG. 4 is a shows venous anatomy and the heart in isolated, schematic form in a sagittal view, with the anterior anatomy on the left side of the Figure. The SVC is shown at 100, with the left brachiocephalic vein at 102 and the right brachiocephalic vein at 104. The right ITV 110 extends inferiorly from its ostium at the right brachiocephalic vein 104. The left ITV 112 extends inferiorly from its ostium at the left brachiocephalic vein 102. The azygos vein 120 extends posteriorly from the SVC 100 and then inferiorly to the right of midline, with the accessory hemiazygos vein shown at 124 and the hemiazygos vein shown at 122. Using this illustration, certain examples follow.

Figure 5:
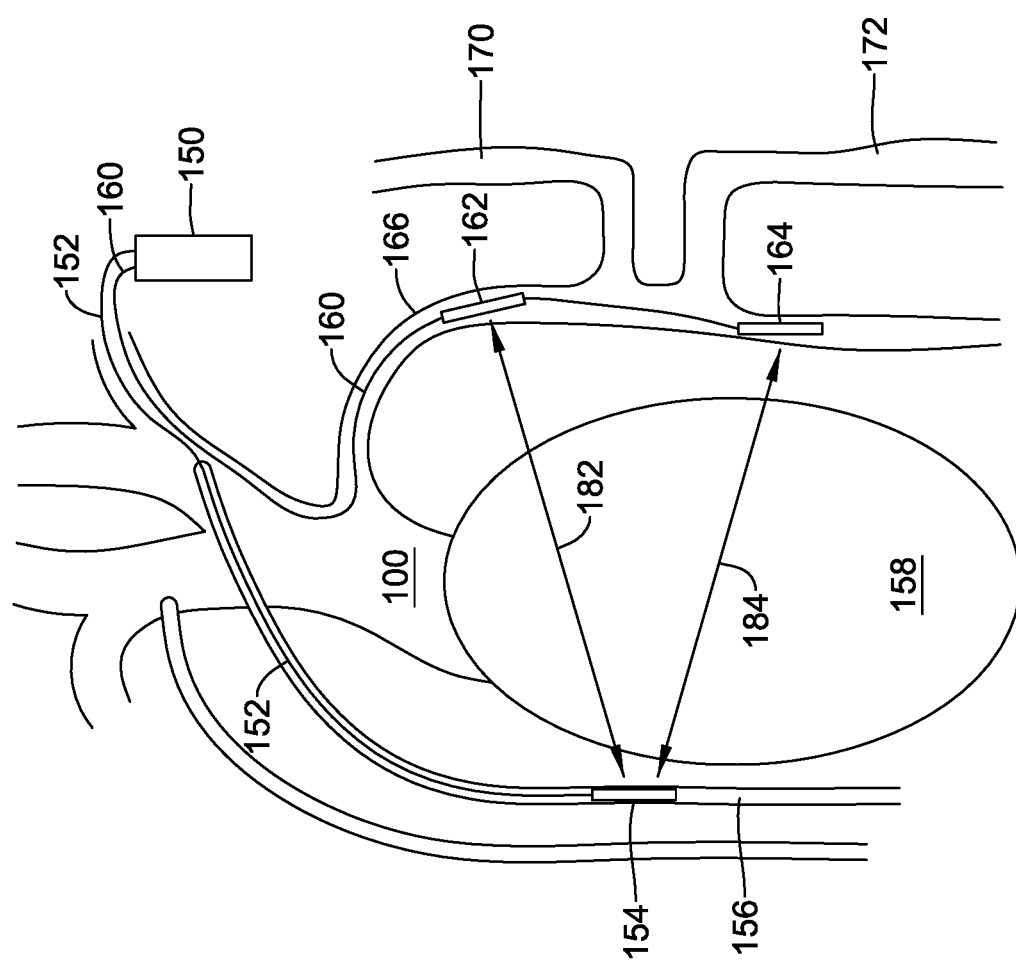
FIGS. 5-6 show illustrative implant locations for some examples.
Figure 6:
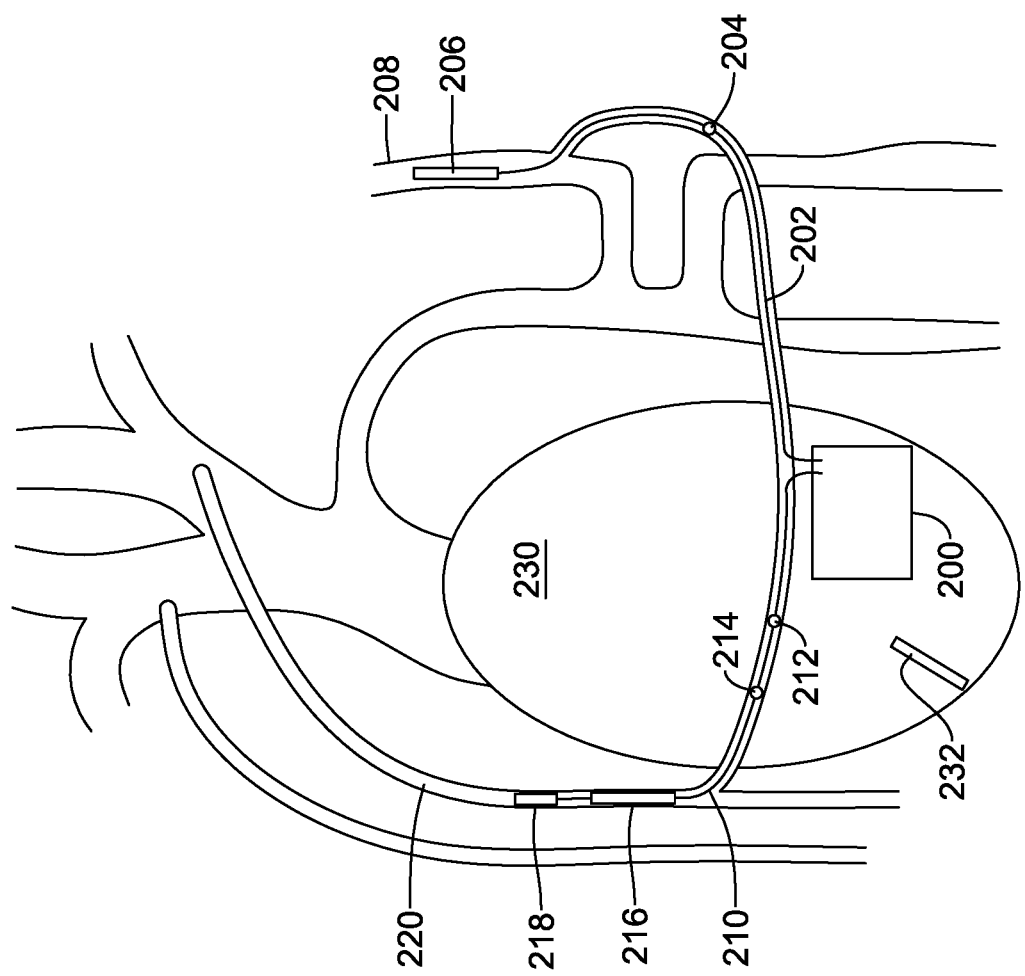

FIGS. 5-6 show illustrative implant locations for some examples. A device canister is shown at 150 and contains the operational circuitry for a cardiac therapy system. Such operational circuitry is known in the art and may include, for example, output circuitry for high and/or low power therapy (defibrillation, cardioversion, pacing, for example), input circuitry for receiving, filtering, and amplifying received signals (such as the cardiac electrical signal) and converting such signals to digital form for analysis by logic and/or processing circuits to identify cardiac cycles, count such cycles, and determine whether various cardiac rhythms and arrhythmias are present. Sensors and communication circuits may be included as well as power supplies such as batteries of various known chemistries. A device may include a microcontroller or microprocessor with associated logic circuits and readable and/or read-writeable memory containing stored instructions executable to perform sensing and other functions as needed and appropriate and well known in the art. Dedicated circuitry, such as one or more application specific integrated circuits, or other analog or digital circuitry, may be included for filtering, analog-to-digital conversion, cardiac cycle detection, signal shape (morphology) analysis, communication, and other purposes without necessarily invoking the use of a controller or processor continuously. State machines and other architectures may be incorporated as well.

In some examples, the output circuitry may comprise a charging circuit such as a flyback transformer circuit, or other circuits using DC:DC conversion (or other suitable methods) to generate a high voltage electrical signal to charge one or more capacitors to a desired therapy level. For example, a transformer with single, double, or even triple tapped secondary winding may be used to couple input current/power to one, two, or three therapy delivery capacitors. In some examples, therapy levels for systems as shown in FIGS. 5-6 may be in the range of, for example, 0.1 to 100 Joules. In other examples, a therapy level may be in the range of about 20 to about 60 Joules. Peak voltages may be in the range of, for example, 400 to about 1400 volts. In other example, a peak voltage may be in the range of about 600 to about 1200 volts. Other voltage and energy range may be used.

The canister 150 will typically include a hermetically sealed housing which may double as or include therapy and/or sensing electrode(s) and an associated header and feedthrough structure to couple to leads 152, 160. The canister 150 implant location shown may be that typically used for transvenous implantable systems, near the left clavicle.

Lead 152 is shown as extending via the brachiocephalic vein into the left ITV 156, with a therapy delivery or other electrode(s) shown schematically at 154. A number of sensing, pacing, coil or other electrodes may be included on lead 152. This position places an electrode 154 anterior to the heart. A lower or higher position relative to the heart 158 may be used as desired.

Lead 160 extends through the brachiocephalic vein and into the SVC and then into the azygos vein 166 and includes at least one therapy electrode. In the example of FIG. 5, the lead 160 includes a first therapy electrode shown at 162 and a second therapy electrode shown at 164. Either or both of electrodes 162, 164 may be included as desired. Such an implantation creates therapy vectors shown at 182, 184. Therapy may be delivered between electrode 154 and either or both of electrodes 162, 164. Sensing may be accomplished similarly. In an example, both of electrodes 162, 164 may be used for ventricular defibrillation purposes as a single electrical node by holding both of 162, 164 electrically common as one pole relative to the ITV electrode at 154. Vector 184 may be used for lower voltage ventricular pacing, if desired, while vector 182 may be used for cardioversion to attempt to terminate atrial fibrillation if needed. Alternatively, vector 184 may serve as a ventricular defibrillation vector without the use of electrode 162.

For purposes herein, a therapy may be delivered between a first electrode and a second electrode with the first electrode serving as anode and the second electrode as cathode, or vice versa. Moreover, therapy may be monophasic or multiphasic such that the use of anode and cathode during a first phase is reversed in a later phase. Waveforms may be current controlled or voltage controlled. Wave shapes may include square waves or ascending or descending amplitudes (ramped or decaying, for example), sinusoidal forms, or any desired shape.

In the example shown the accessory hemiazygos vein 170 is not traversed or used; likewise the hemiazygos vein 172 is not used. In other examples, lead 160 may be advanced into one of veins 170, 172, or both veins may be used if lead 160 is bifurcated or if two azygos/hemiazygos leads are used.

The lead placements shown may be achieved by the use of a guidewire advanced to a desired position, with the leads placed over the guidewire. In other examples, a steerable lead may be used, or a lead may be placed by advancement using a steerable stylet. Fluoroscopy or other visualization may be used as desired or needed.

FIG. 6 shows another example. Here, a left axillary canister position is used to place the canister 200 at a position similar to that used for the Emblem S-ICD System™ from Boston Scientific. From the left axilla, an intercostal vein 202 can be accessed and used for advancement of a lead 204 posteriorly to the accessory hemiazygos vein 208, placing a therapy or other electrode as shown at 206. In other examples the more inferior hemiazygos vein may be used instead. A second lead 210 is advanced in an anterior and medial direction to the left ITV 220, to place a therapy electrode as shown at 216. Additional sensing or pacing electrodes may be included on lead 210 as shown at 212, 214, and 218; rather than electrodes, other sensors (such as accelerometers or heart sound sensors) may be placed. This implantation places the heart 230 squarely between the therapy delivery electrodes 206, 216.

Therapy for defibrillation, cardioversion, and/or pacing purposes may be delivered between anterior electrode 216 and posterior electrode 206. The canister 200 may be used as an additional electrode in electrical common with either of 206 or 216, and/or may serve as an indifferent electrode, or may be omitted from therapy delivery as desired. If desired, one or more additional devices such as a leadless cardiac pacemaker (LCP) 232 may be placed in or on the heart 230 to provide additional pacing options or other functional inputs such as serving to provide cardiac rate information.

In other examples, lead 202 may be advanced across the midline to the azygos vein after entering the hemiazygos vein or accessory hemiazygos vein, as desired.

Referring to both of FIGS. 5 and 6, a number of pacing, defibrillation, and/or sensing vectors may be defined. For example, pacing vectors may include:
  Between the right or left internal thoracic vein and the azygos vein;
  Between the right or left internal thoracic vein and the hemiazygos vein;
  Between the right or left internal thoracic vein and the accessory hemiazygos vein;
  Between two electrodes within the same vein, such as between two electrodes in the right or left ITV or in one of the azygos, hemiazygos, or accessory hemiazygos veins;
  Between an electrode on a pulse generator canister and an electrode or plural electrodes in one or more of the azygos, hemiazygos, or accessory hemiazygos veins or the right or left ITV;
  Any of these combinations may be further adjusted by using an intercostal vein, if desired, to direct current/field in a more lateral direction.

Within such vectors, a selection of superior or inferior positioning within the selected veins may be adjusted to obtain a pacing vector preferentially intersecting a selected atrial or ventricular chamber. For example, pacing between the right internal thoracic vein and the azygos vein at a relatively superior position, level with the atria, may target the right atrium. Pacing therapy delivered between the left internal thoracic vein and the hemiazygos vein may direct the therapy generally to the left ventricle. It may be noted that the left internal thoracic vein may overlie the interventricular septum, allowing pacing of both chambers at once. In some examples, a sensing vector using an electrode in the right or left internal thoracic vein may be used to detect P-waves to support cardiac resynchronization using, for example, a pacing output electrode directed to a ventricular location such as a pacing therapy delivered using an intracardiac pacemaker or a pacemaker electrode in an internal thoracic vein, an azygos, hemiazygos, or accessory hemiazygos vein, or an intercostal vein. Subcutaneous, transvenous, and/or epicardial electrodes may be used in further combinations.

Defibrillation therapy may likewise be delivered using several such combinations:
  Between the right or left internal thoracic vein and the azygos vein;
  Between the right or left internal thoracic vein and the hemiazygos vein;
  Between the right or left internal thoracic vein and the accessory hemiazygos vein;
  Any of these combinations may be further adjusted by using an intercostal vein, if desired, to direct current/field in a more lateral direction.

For defibrillation, one consideration may be whether a sufficient mass of cardiac tissue is stimulated in a given configuration. The shock vector may in some examples be different from that of pacing by, for example, delivering diagonally across the torso between the left internal thoracic vein and the azygos vein for defibrillation with pacing delivered between the right internal thoracic vein and the azygos vein. Therapy may be delivered using a combination of three or more electrodes such as:
  With defibrillation coil electrodes in each of the right and left internal thoracic veins and the azygos vein, the hemiazygos vein, or the accessory hemiazygos vein, where the coils in the internal thoracic veins are held electrically in common;
  With defibrillation coil electrodes in the azygos vein and one (or both) of the hemiazygos vein and/or accessory hemiazygos vein in common, as an opposing pole to a defibrillation electrode in either the right or left internal thoracic vein; and
  In a four electrode system, a first pole may use defibrillation electrodes in each of the right and left internal thoracic veins electrically in common, electrically opposed to defibrillation electrodes in each of the azygos vein and one of the hemiazygos or accessory hemiazygos veins.

Where more than two electrodes are used, voltage and/or current control may be used to allocate energy to specific electrodes or to target specific tissue using the concept of current steering. For example, in FIG. 5, a defibrillation therapy output may be manipulated to deliver a greater quantity of current through electrode 164 than through electrode 162 to steer current toward the ventricles. Such steering may use current control (such as a current mirror design), or may use voltage control by coupling a lower peak voltage to electrode 162 than to electrode 164, or by terminating therapy delivery through electrode 162 prior to terminating therapy delivery through electrode 164. A similar concept maybe used in FIG. 6 to manage output power through electrodes 216 and 218. It should be noted that the heart in each of FIGS. 5 and 6 is shown in a more inferior position than may be used in some examples; for example, the canister 200 and one or more of the therapy delivery electrodes may be positioned more inferior relative to the apex of the heart. The device canister 200 may optionally be used as an additional electrode for therapy delivery purposes. In some examples, the concept of steering may be accomplished by determining which of several electrodes to include in therapy delivery, rather than by controlling the voltage or current.

Sensing may be achieved between electrode pairs, for example, similar to the pacing combinations noted above. Sensing may also be performed within any one of the vessels noted as by, for example, having first and second sensing electrodes in one of the internal thoracic veins. Superior and inferior positioning may be used to achieve chamber specific sensing vectors (ventricular or atrial, for example).

In an alternative example, a subcutaneous electrode may take the place of a therapy delivery electrode in the internal thoracic vein. For example, therapy may be delivered between a first electrode disposed in least one of the azygos, hemiazygos, or accessory hemiazygos veins, and a second electrode disposed subcutaneously on the anterior chest of the patient such as in a parasternal position. Pacing and/or sensing electrodes may also be disposed, in this example, in an internal thoracic vein.

In a still further alternative, a subcutaneous electrode may take the place of a therapy delivery electrode in the azygos, hemiazygos, or accessory hemiazygos veins. For example therapy may be delivered between a first electrode disposed in one of the internal thoracic veins and a second electrode disposed subcutaneously on the posterior thorax of the patient over the ribcage.

FIGS. 7-10 show illustrative electrode/lead designs; these designs may be used in any of the ITV, intercostal vein, azygos vein, hemiazygos vein, or accessory hemiazygos vein. Generally speaking, the coil electrodes shown may be used for high power therapy delivery such as defibrillation and/or cardioversion, while ring and tip electrodes may be used for sensing cardiac signals. Rather than a coil electrode, a defibrillation "electrode" may be made up of a plurality of electrode rings ganged or multiplexed together to form a common electrical pole. Pacing therapy may be delivered using any of the electrodes shown as desired. Each such electrode may be used for additional purposes; for example, a coil electrode may be used for sensing as well, and a ring or tip electrode may be used for high power therapy output. The arrangements shown, or other arrangements, may be used in the above or below examples as desired.

Figure 7:
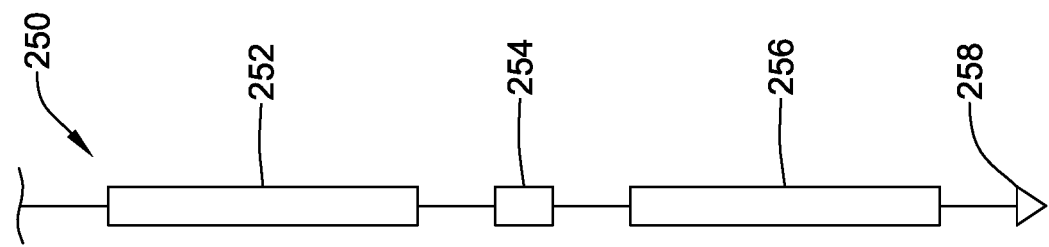

In FIG. 7, a lead 250 includes a proximal coil electrode 252, a proximal ring electrode 254, a distal coil electrode 256, and a distal tip 258 which may include an anchoring mechanism such as a screw or tine and/or which may include another electrode. The anchoring mechanism may be deployable and retractable by, for example, using a screw or tine which may be extended and/or retracted by actuation near or at a proximal end of the lead 250.

Figure 8:
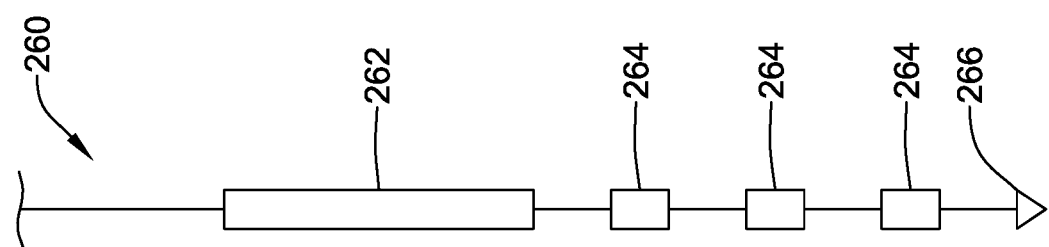

In FIG. 8, a lead 260 includes a proximal coil electrode 262 and a plurality of distal ring electrodes 264, again with a distal tip 266 that may include an anchoring mechanism and/or additional electrode.

Figure 9:
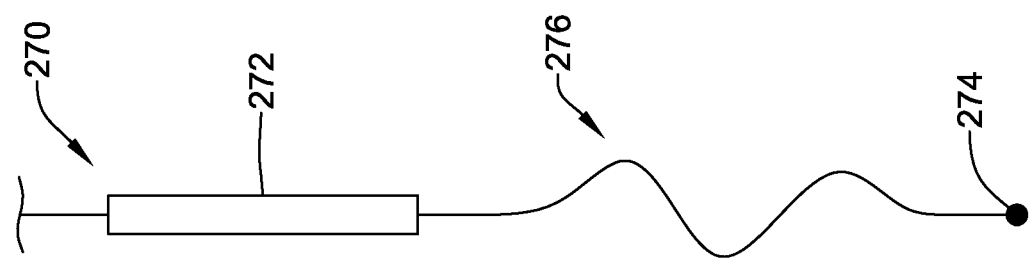

In FIG. 9, lead 270 includes a coil electrode 272, distal to which is an anchoring section 276 shown as a spiral or helix with a distal tip at 274. The anchoring section 276 may be used to anchor in a desired blood vessel; for implant, this portion 276 may be held in a more linear/straight configuration using a stylet, and after removal of the stylet the helical shape may be assumed using shape memory metal or pre-forming of the lead shape.

Figure 10:
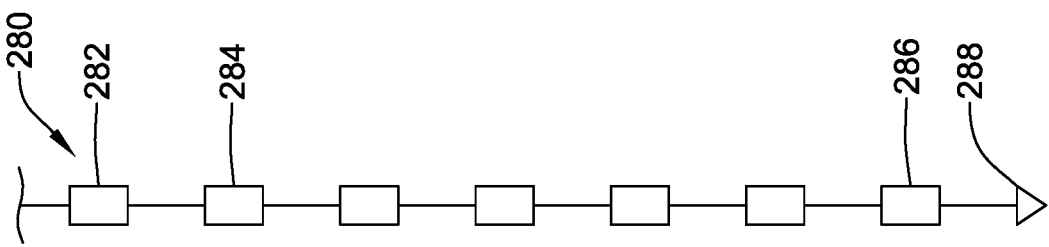
FIGS. 7-10 show illustrative electrode/lead designs.

In FIG. 10, a lead 280 includes a plurality of ring electrodes 282, 284 . . . 286 and a tip 288 which may serve as an additional electrode. In use, this approach allows various and specific sensing and/or pacing therapy options to direct sensing or pacing therapy to different chambers of the heart, for example. For a higher power output, some or all of the ring electrodes can be ganged together electrically in common.

Figure 11:
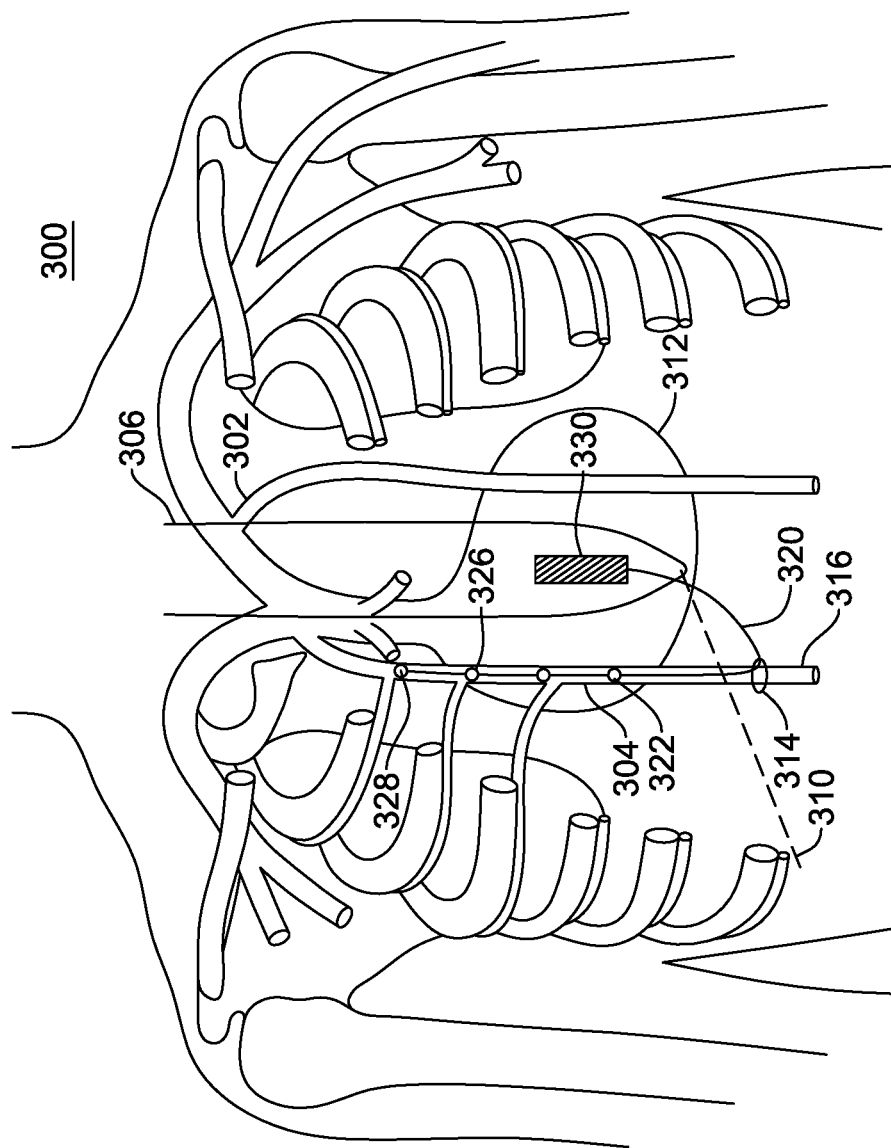
FIGS. 11-12 show devices with internal thoracic vein sensors.
Figure 12:
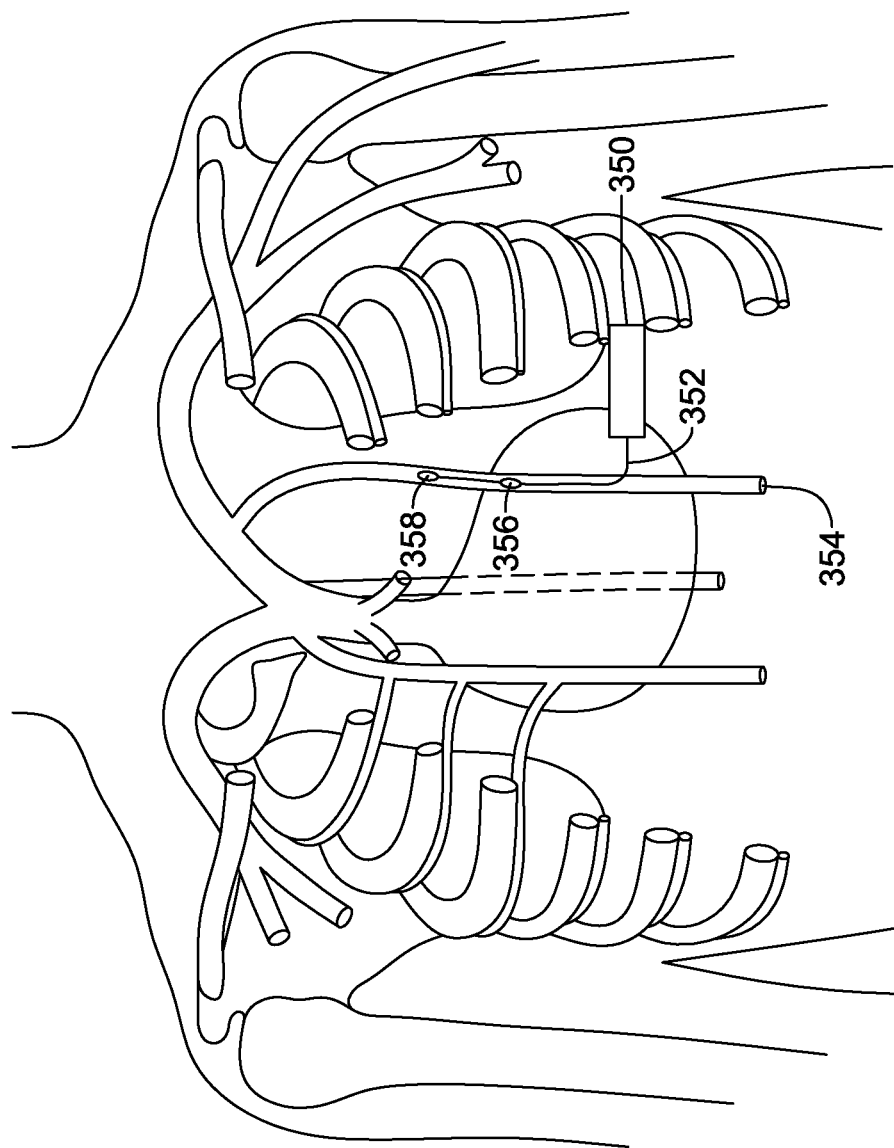

FIGS. 11-12 show devices with internal thoracic vein sensors. In the example 300 of FIG. 11, the patient is shown having a left ITV at 302 and a right ITV at 304. The sternum of the patient is shown in outline at 306. A device 330 is implanted over the sternum 306 with a lead 320 extending thereform into the superior epigastric vein 316 inferior to the lower rib margin shown at 310. The lead is advanced superiorly into the right ITV 304 and has electrodes and/or sensors thereon as shown at 322, 324, 326 and 328. A single sensor may instead be provided. The sensors may be used by the device 330 to obtain information regarding pressure, heart sounds, cardiac motion, patient motion, blood flow, temperature, or other data, as desired. Various examples of sensor types are further discussed below. The device 330 may include therapy output capability if desired, or may only be a monitoring apparatus. Additional leads or electrodes may be provided, and other implant locations may be used. In an alternative approach, the musculophrenic vein at the lower rib margin may be accessed instead of the superior epigastric vein 316.

FIG. 12 shows another example. Here, a device canister 350 is implanted in an intercostal space with a lead shown at 352 entering the left ITV 354. Such entry may be achieved in a parasternal location between two ribs using a Seldinger-type technique, in which an ultrasound needle can be used to first pierce into the left ITV 354, with a guidewire passed therethrough; the guidewire can be held in place as the needle is removed, and an introducer passed over the guidewire to allow passage of the lead 352. Here, the lead 352 is shown with two electrodes or sensors at 356, 358. More or fewer electrodes or sensors may be used. Other examples use sensors which are disposed without the use of a lead.

Figure 13:
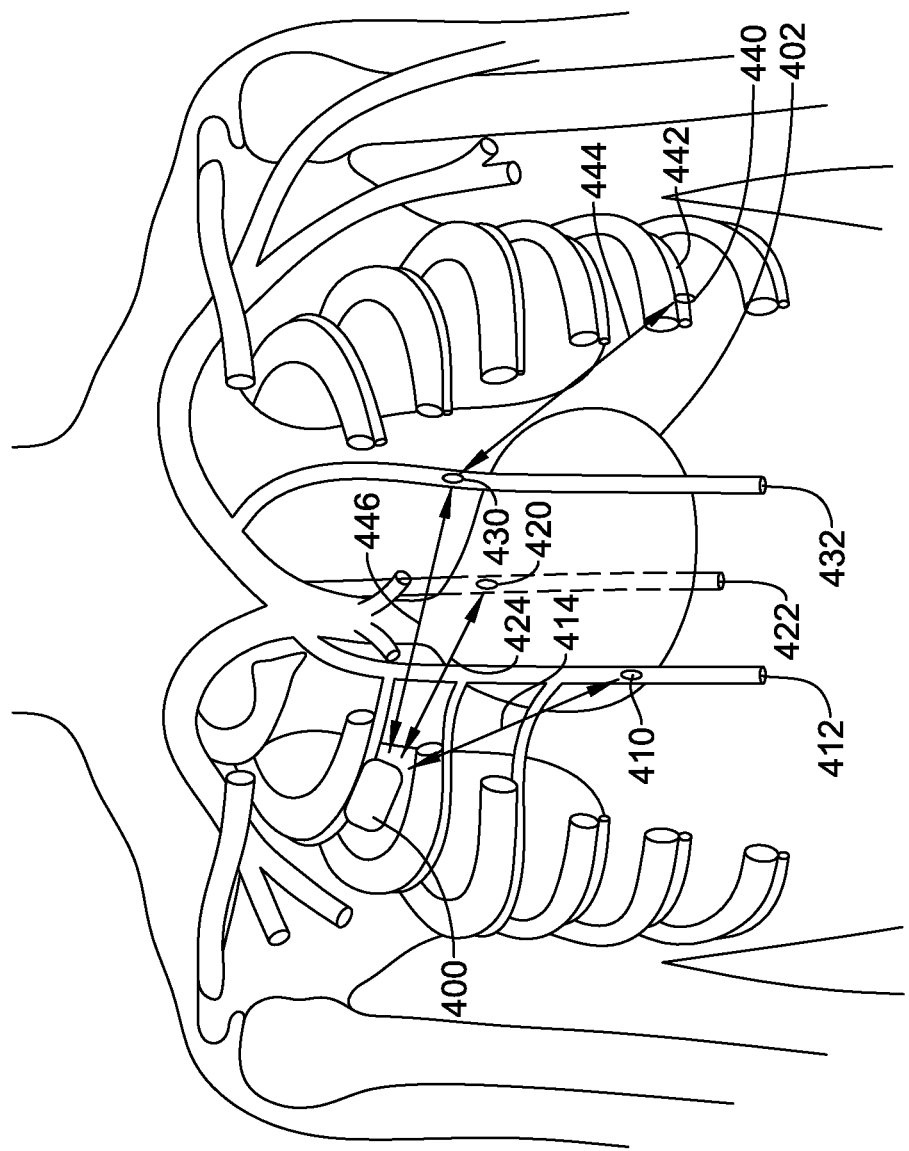
FIGS. 13-14 show systems with several intravenous sensors.
Figure 14:
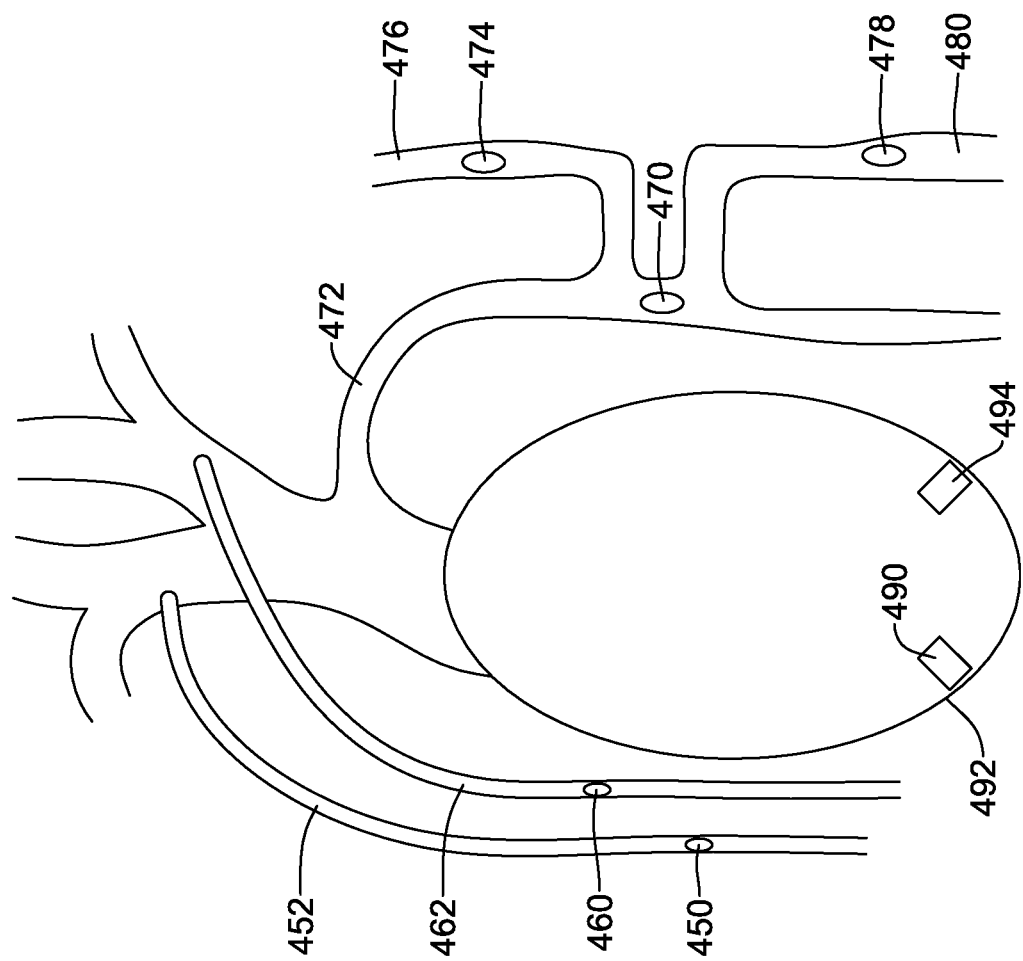

FIGS. 13-14 show systems with several intravenous sensors. In FIG. 13, a plurality of sensors are placed in the patient. A receiver for sensing data is shown at 400 for illustrative purposes and may be an implantable or wearable monitor. In other examples, the "receiver" 400 may instead be an implantable or wearable therapy apparatus, such as a transvenous or subcutaneous defibrillator.

Sensors are shown at various places, including a sensor 410 in the right ITV 412, a sensor 420 in the azygos vein 422, a sensor 430 in the left ITV 432, and a sensor 440 in an intercostal vein 442. Communication may be performed between the individual sensors and the receiver 400, such as indicated at 414, 424, 446. In some examples, the sensors may also communicate with one another and/or one or more sensors may serve as a relay for sensing data. For example, sensor 440 may communicate as indicated at 444 to sensor 430 which conveys data back to the receiver 400.

The sensors 410, 420, 430, 440 may be independently powered by having batteries (primary or rechargeable, as desired). In some examples, one or more sensors may be activated using RF, ultrasonic, or inductive energy. For example, the receiver 400 may issue an addressed RF, ultrasonic, or inductive signal that activates one or more sensors 410, 420, 430, 440 to generate a responsive output.

In the example of FIG. 13, various sensors are disposed relative to the heart 402 without necessarily touching or residing in or on it. Additional sensors or devices may also be placed in or on the heart if desired, such as shown in FIG. 14.

FIG. 14 shows another example. Here, the various sensors include a sensor 450 in the right ITV 452, a sensor 460 in the left ITV 462, a sensor 470 in the azygos vein, a sensor 474 in the accessory hemiazygos vein 476, and a sensor 478 in the hemiazygos vein 480. An LCP is shown as well at 490, in the right ventricle of the heart 492; a second LCP may be placed as well as shown at 494, in or adjacent to the left ventricle 494, as desired. Additional locations may include, for example, a coronary vein such as the coronary sinus, in which an LCP or a sensor may be placed.

The examples of FIGS. 13-14 show numerous sensors. In various examples, only one or two sensors may be used; in other three, four, five or more sensors may be used. The sensors may be of the same type or may be of different types, with various options shown below in FIG. 16. Though not shown in FIGS. 13-14, the system may further include a defibrillation such as a subcutaneous defibrillator, which may obtain information from the various sensors shown to facilitate analysis of the patient's condition and, as needed, to support determinations of whether therapy ought to be delivered.

Figure 15:
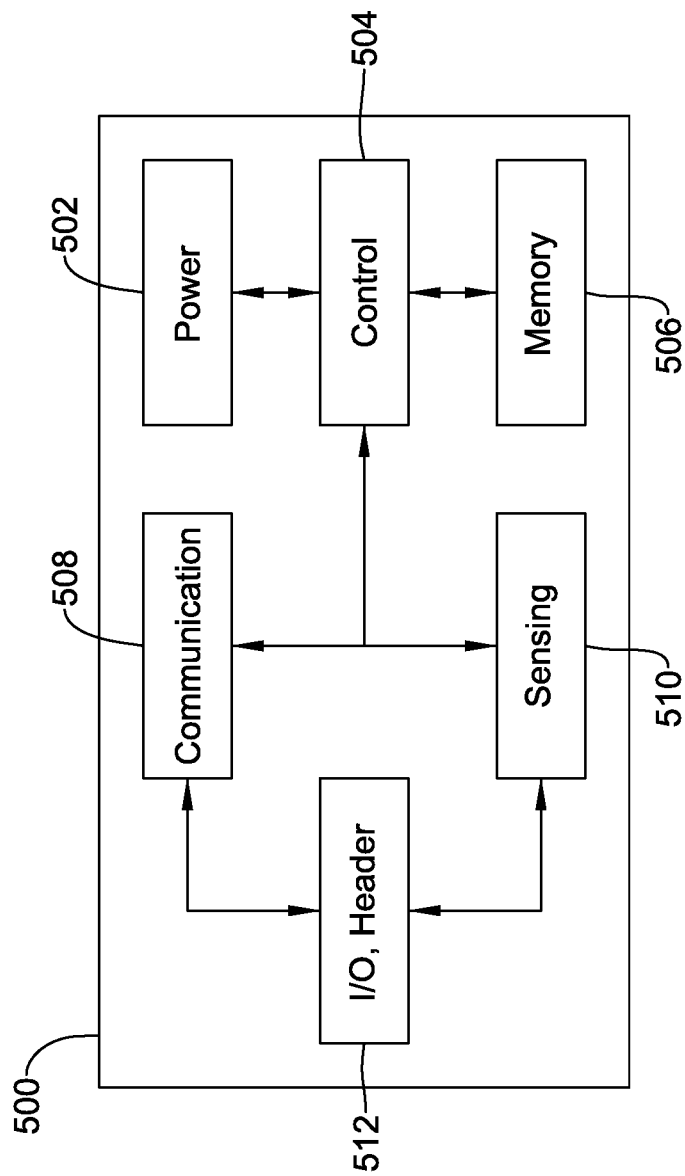
FIG. 15 shows an illustrative implantable device operational circuitry.

FIG. 15 shows an illustrative implantable device operational circuitry. A housing 500 is shown as containing a number of elements; not all of these items are required in various examples. A power subcircuit, such as a battery or capacitor may be included as indicated at 502. If the device is rechargeable or adapted to receive power remotely, additional charging elements, such as an inductive coil, an antenna, a piezoelectric element, or an ultrasound transducer may be included as well. A control circuit is shown at 504 and may be a state machine or a controller, or may simply be a set of logical circuits. Some examples may include a memory 506 to store operational instructions and/or sensed data for later offloading. A communication circuit is shown at 508 and may be adapted for use in conducted, inductive, RF, sonic/ultrasound, optical, or any other suitable communication medium.

Figure 16:
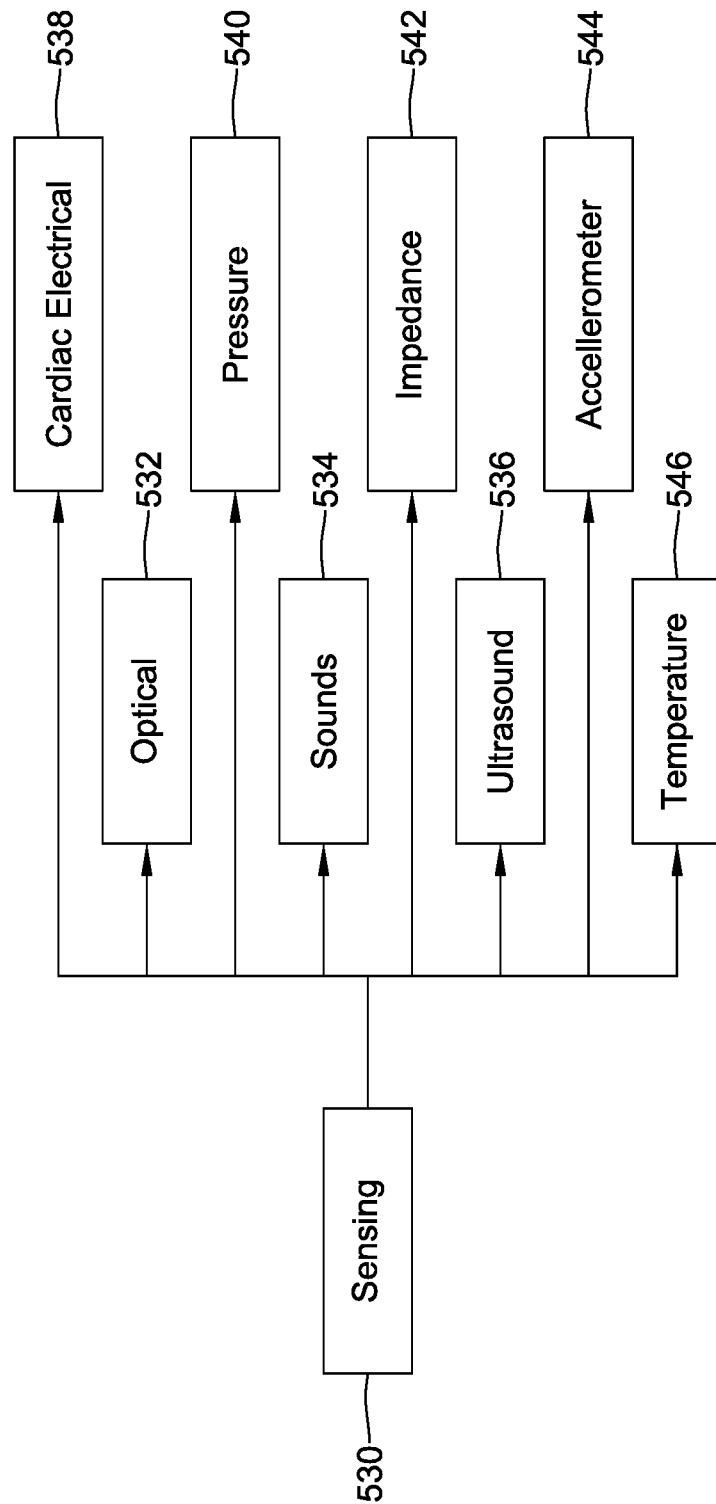
FIG. 16 highlights a number of sensors and sensor types.

A sensor is included as indicated at 510; FIG. 16 shows various sensor alternatives. If needed, an input/output or header may be included as indicated at 512 to connect to a lead or one or more electrodes or transducers.

The device may range from sophisticated, as shown, to far more simple configurations. For example, a sensor may be adapted to be responsive to RF or ultrasound interrogation and may include only the communication 508 and sensing 510 blocks, allowing for a very small footprint that may be implanted in a vein as shown in FIGS. 13-14. Alternatively the sensor may use more space as shown by FIGS. 11-12 and may include all of the functional blocks shown. Given the availability of very small LCP architectures, a sensor may use conducted communication to provide output data with a lifetime of several years while including most or all of the functional blocks indicated in FIG. 15.

FIG. 16 highlights a number of sensors and sensor types. A sensing subcircuit 530 may include, for example, an optical sensor 532. An optical sensor 532 may be used to obtain an estimation of oxygen saturation, hemoglobin, and/or hematocrit, for example; placement in the vascular structures shown would allow direct access to flowing blood for such purposes. A sensing subcircuit 530 may include, for example, a sound sensor 534 that can capture heart sounds or vibrations, indicating various phases of cardiac function. A heart sound sensor can allow assessment of, for example, cardiac contractility, filling, and/or systolic time intervals to allow resynchronization. A sensing subcircuit 530 may include, for example, an ultrasound sensor 536; ultrasound sensing may be used to estimate venous blood velocity and/or thoracic fluid levels. Ultrasound monitoring may include using a sensing circuit 530 to receive ultrasound generated elsewhere in the patient, or may be used to both generate and receive ultrasound signals. A sensing subcircuit 530 may include a cardiac electrical signal sensing circuit 538 to extract heart rate, heart rate variability, cardiac signal frequency content, or other factors. Respiration data may be determined from sensor signals that are sensitive to breathing such as impedance, acceleration, or pressure, for example.

A sensing subcircuit 530 may include, for example a pressure signal 540. It may be noted that pressure and sound may be related and are largely differentiated by frequency content; one pressure sensor may capture both sounds and pressure data. Pressure data may include, for example, pulsations in adjacent arteries (the ITV is adjacent to the internal thoracic artery, for example) to determine pulse pressure and variations thereof. Pressure data may also be low pass filtered at long time constants, by the sensor itself or by an associated data receiver, to determine measures of venous congestion. Plural, spaced sensors, such as on a lead or separate sensors in communication with one another or with a receiver, may be used to determine pulse transit time, for example.

A sensing subcircuit 530 may include, for example, impedance measurements 540. Impedance may be measured by generating a test or therapy signal between two electrodes and monitoring for electrical field strength at one or more additional positions. This allows identification of the amount, or changes in, thoracic fluid content using resistive and reactive frequency components. Stroke volume may also be estimated. In a near field, a single sensor may generate an output current or voltage to measure blood conductivity, which can be used to estimate hematocrit and/or hemoglobin levels.

A sensing subcircuit 530 may include, for example, an accelerometer 544 to measure cardiac sounds and/or vibrations, lung sounds or vibrations, displacement of the thoracic wall (such as by ballistocardiography), thoracic activity, patient activity, and/or thoracic posture/position. In addition, the provision of extra sensing of any of these types may be used to aid in filtering out noise signals from various sources, whether electrical, sonic, motion, or otherwise.

A sensing subcircuit may also be used to sense temperature as indicated at 546. For example, temperature can be used as a measure of patient activity.

One or more sensors may be included in a single apparatus, and a system may also include a plurality of sensors of the same or different types.

FIGS. 17A-17B, 18A-18B, 19A-19C, 20A-20C, and 21A-21C show illustrative implantation and anchoring approaches.

Figure 17A:
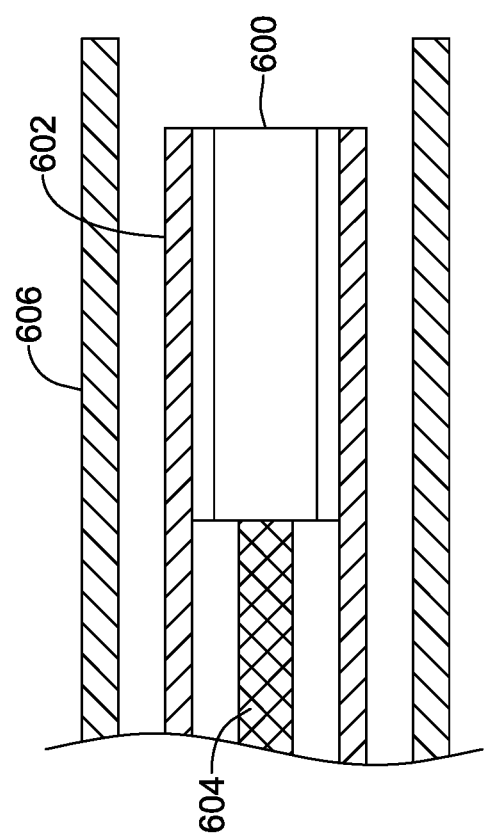
FIGS. 17A-17B, 18A-18B, 19A-19C, 20A-20C, and 21A-21C show illustrative implantation and anchoring approaches.
Figure 17B:
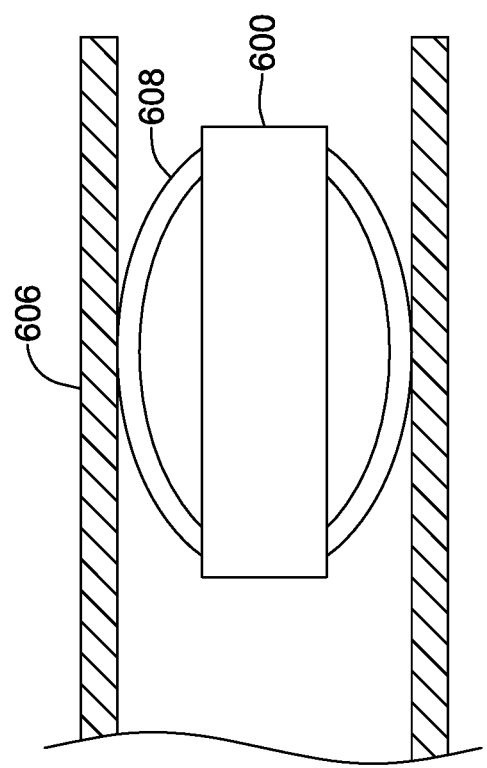

FIG. 17A shows implantation of a device 600. For implantation, the device 600 is placed in a delivery catheter 602 having a push rod 604. The device 600 is advanced to a desired location in blood vessel 606. The push rod 604 is used to push the device 600 out of the delivery catheter 602. As shown in FIG. 17B, this pushing motion releases anchoring members 608, which engage the walls of the vessel 606, fixing the device in place. The anchoring members 608 may be formed of a biocompatible spring material such as a stainless steel, titanium, or biocompatible polymer. A shape memory metal may also be used if desired.

Figure 18A:
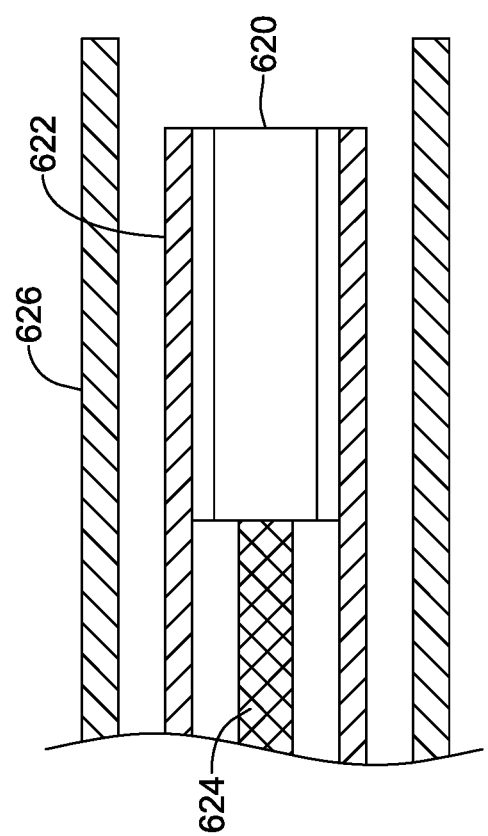
Figure 18B:
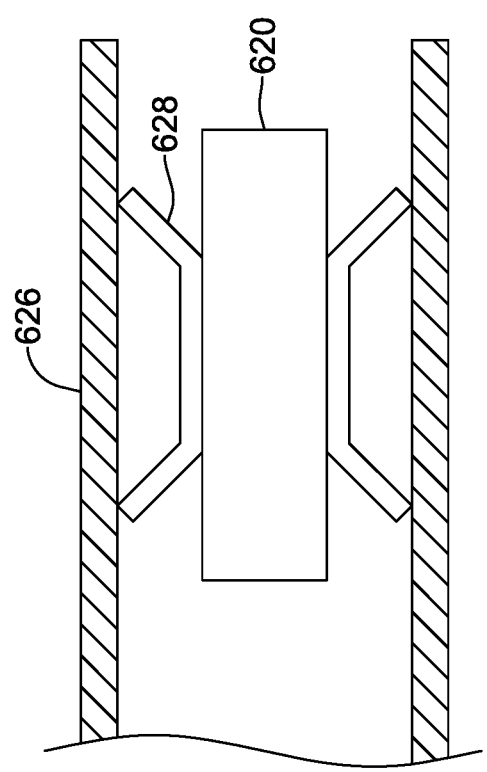

FIG. 18A shows another example. The device 620 is again disposed in a delivery catheter 622 having a push rod 624 and advanced to a desired position in a blood vessel 626. The push rod 624 is used to push the device 620 out of the delivery catheter 622, releasing anchoring members 628, this time shown as a plurality of tines, as shown in FIG. 18B. Fewer or more tines may be used, as desired.

Figure 19A:
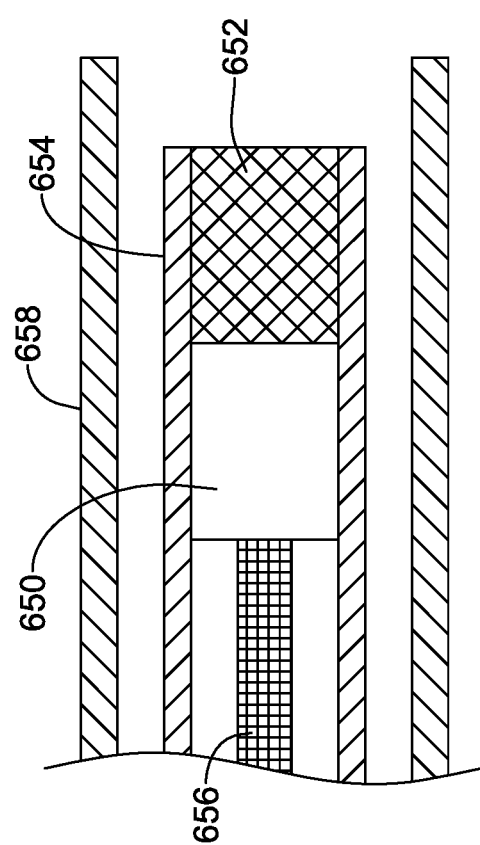
Figure 19B:
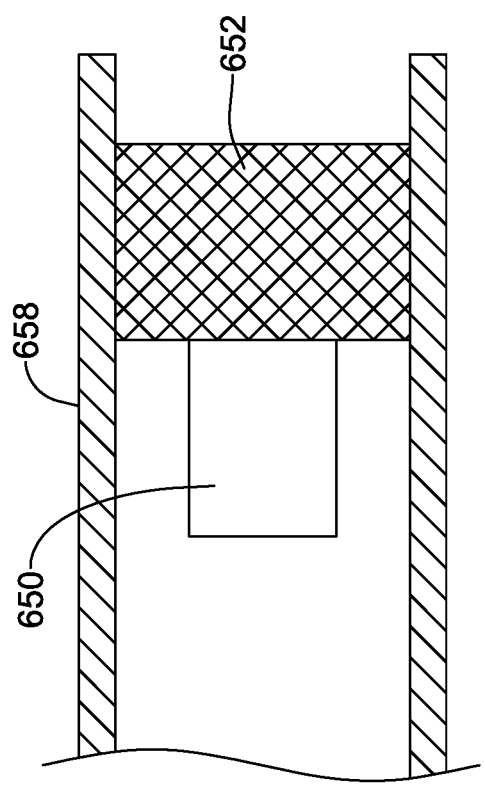
Figure 19C:
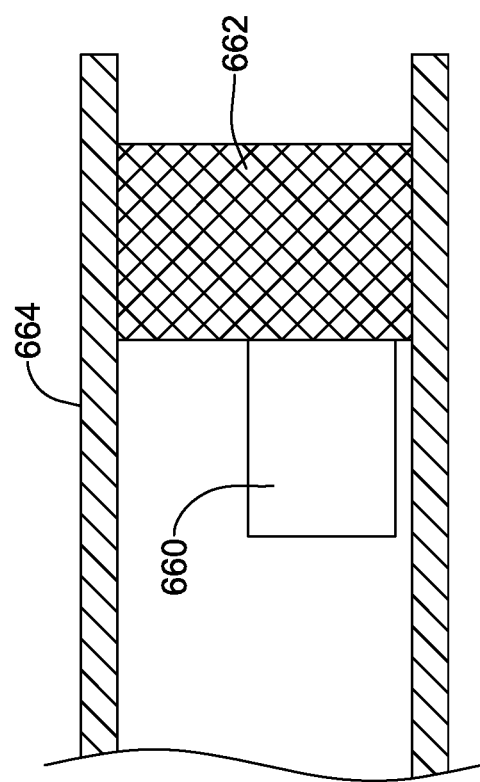

FIG. 19A shows another example. Here, the device 650, with an anchoring member 652, is disposed in a delivery catheter 654, again with a push rod 656. The device is advanced to a desired location in the blood vessel 658. As shown in FIG. 19B, the push rod 656 has been used to push the device 650 out of the delivery catheter 654, allowing the anchoring member 652 to expand as shown to engage the walls of the vessel 658. The anchoring member 652 may be, for example, a self-expanding and, optionally, repositionable stent. The device 650 may be suspended centrally in the anchoring member 652, as shown in FIG. 19B. FIG. 19C shows an alternative in which the device 660 is secured along a side of the anchoring member 662 to hold device 660 generally against an edge of the vessel 664. This may allow a sensor to be directed outwardly from the vessel 664 in a preferential manner, or may allow a sensor to be directed toward the center of the vessel 664 to allow monitoring of blood flow therethrough.

Figure 20A:
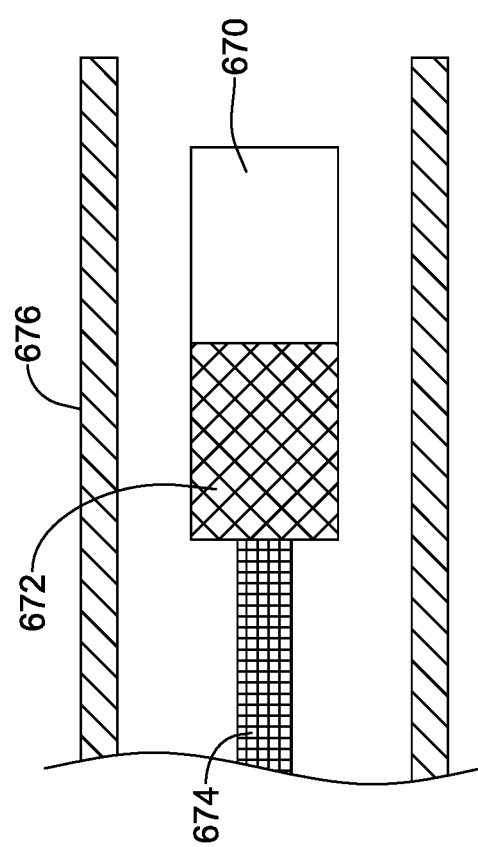
Figure 20B:
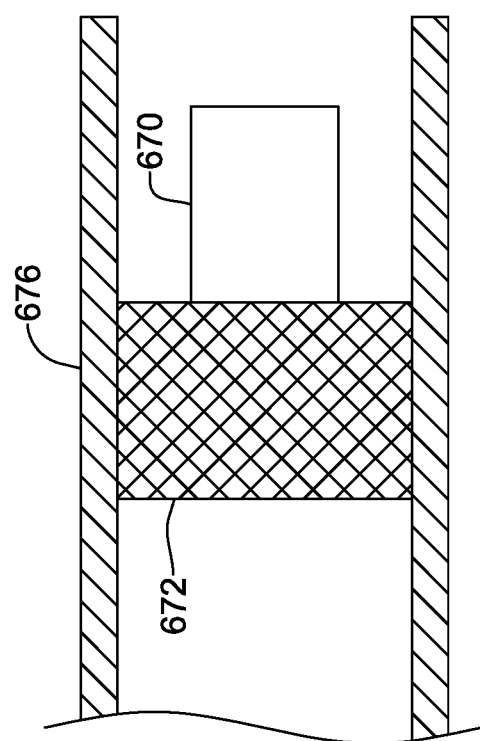
Figure 20C:
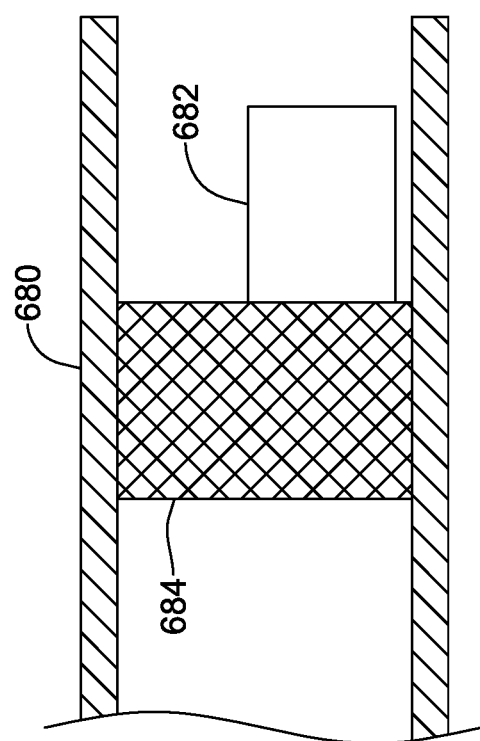

FIG. 20A shows another example. Here, the device 670 is at the distal end of a delivery catheter 674 with a stent 672 for anchoring purposes disposed over and secured onto an expandable balloon. The device is advanced to a desired location in vessel 676 and the balloon is expanded using known techniques for stent placement. The placed device is as shown in FIG. 20B, with the stent 672 now expanded to engage the vessel walls 676, securing the device 670. In FIG. 20B, the device is generally suspended central to the stent. FIG. 20C shows an alternative in which the device 682 is disposed adjacent a wall of the blood vessel 680 on the expanded stent 684.

Figure 21A:
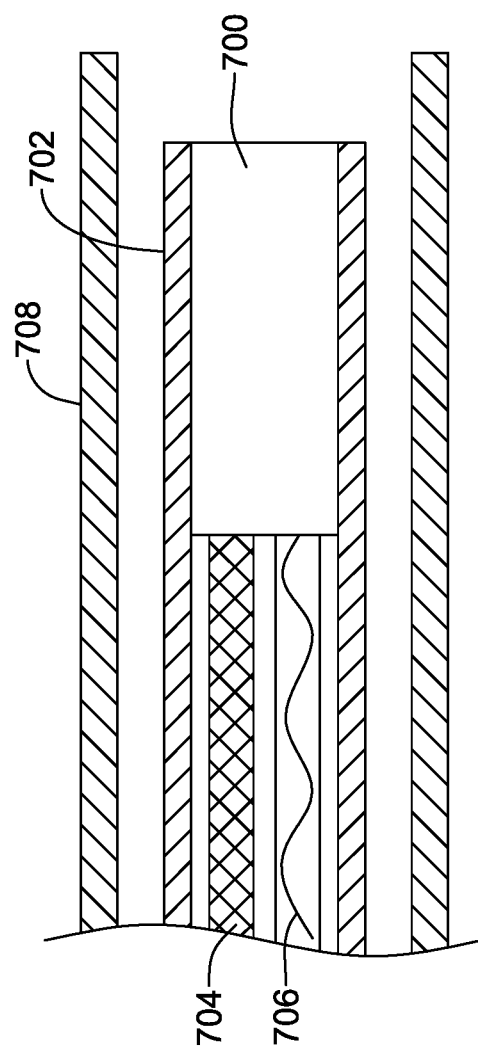
Figure 21B:
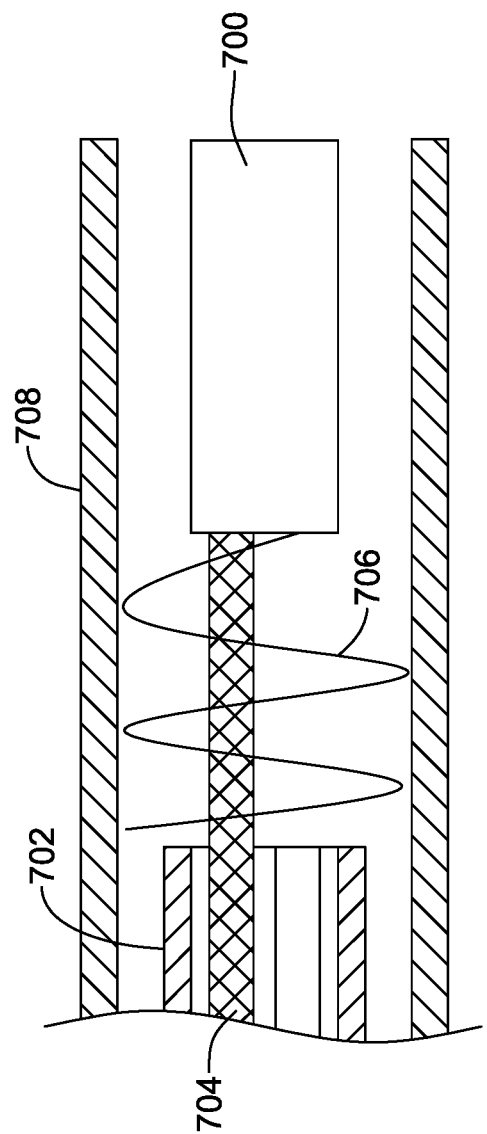
Figure 21C:
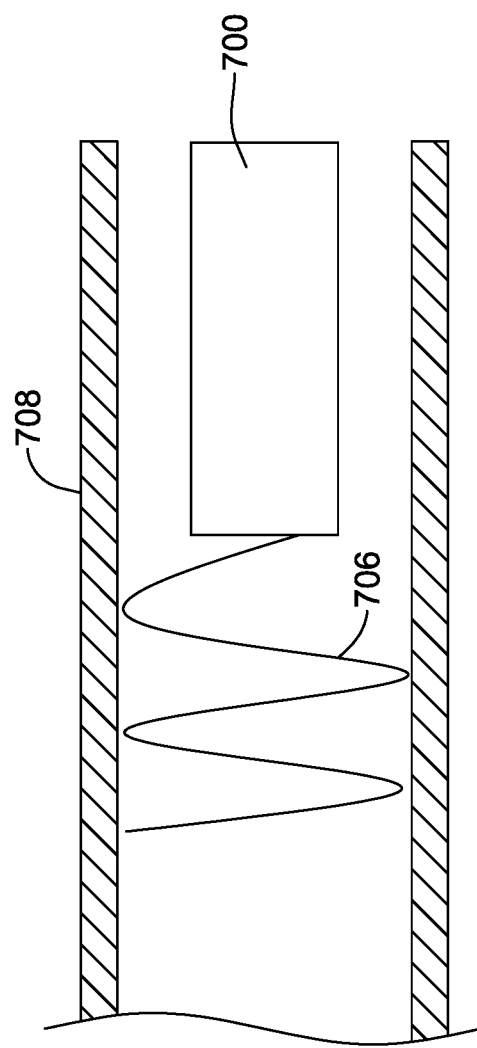

FIGS. 21A-21C show another example. Here the device 700 is shown in a delivery catheter 702. The delivery catheter 702 includes a push rod at 704 and a lumen to receive a pigtail 706 for the device 700. The device 700 is advanced to a desired location in the vessel 708. As shown in FIG. 21B, the push rod 704 pushes the device 700 out of the distal end of the delivery catheter 702. This movement allows the pigtail to expand into a helical shape, engaging the vessel 708. As shown in FIG. 21C, the delivery catheter is removed and the pigtail 706 secures the device 700 at a desired place in the vessel 708.

In some examples, devices as shown in FIGS. 17A-17B, 18A-18B, 19A-19C, 20A-20C, and 21A-21C may be specially adapted for placement and/or use in a particular location. For example, the devices may comprise anchors adapted to interact with a venous wall, or sized for a particular location in a patient's vasculature. In an example, a stent, coil or other expandable member may be sized to securely interact with the walls of a blood vessel or valve within a blood vessel by the use of a size that approximates or is slightly smaller or larger than a target vessel. For example, an ITV located device may have an outer diameter of 3 to 10 French, with smaller diameters for placement more inferior in the blood vessel. In another example, a device for placement in an intercostal vein may be sized in the range of about 2 to about 6 French, for example. The azygos vein is typically larger, with diameter in the range of up to 1 cm, and so placement in a tributary thereto may be used in some instances to allow use of a lesser diameter placement or anchoring member. A stent-type placement, including that shown in FIGS. 20C and 21C, for example, may be used, though the other placements shown may also serve in the azygos vein. Larger or smaller sizes may be used as desired.

In some examples, devices as shown in FIGS. 17A-17B, 18A-18B, 19A-19C, 20A-20C, and 21A-21C may be used in conjunction with an implantable device as shown above in FIGS. 5, 6, 11 and/or 12. In such examples, one or more electrodes on one or more leads may be used for selected therapy delivery, while one or more devices that are not on a lead are separately implanted in the patient to allow additional data gathering from additional locations. Thus, for example, an implantable device as shown in FIG. 5 or 6, above, may be used in conjunction with a device for implantation in the patient's right ITV to provide an additional sensing view of the patient's heart. The additional device may supplant the need for a sensor on a lead (such as sensors 212, 214 in FIG. 6), or may instead be used as an additional such sensor. For example, if the flow of blood is to be detected, it may be useful to place a sensor in a location where blood flow is unaffected by the lead(s) 202, 210, such as by placing an optical sensor in a tributary to the azygos vein, allowing placement in a location adjacent a large blood vessel without being in the flow of blood itself. Other combinations and specific examples may be used instead.

Figure 22:
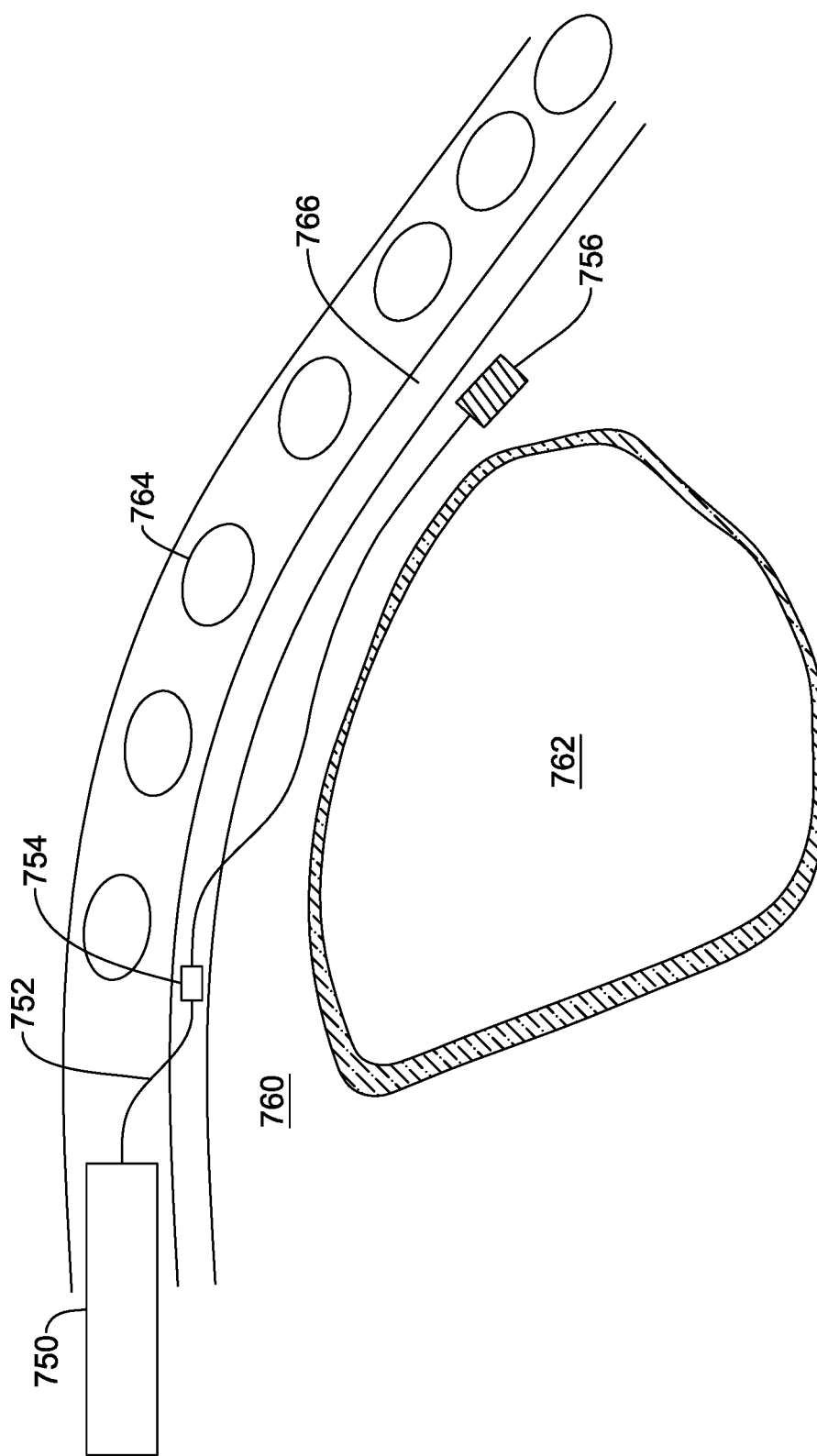
FIG. 22 shows another implant location for one or more sensors.

FIG. 22 shows another implant location for one or more sensors. The figure shows a sagittal section from the side, with the heart at 762 behind the ribs 764, illustrating the left internal thoracic vein at 766 and showing, generally, the mediastinum. In this example, a device canister 750 is implanted in an abdominal location, with a lead 752 entering the ITV 766, and having a sensor or electrode at a first location 754. The lead 752 then exits the ITV and enters the mediastinum. An additional sensor 756 is located on the lead 752 in the mediastinum.

In another example, the sensor 756 may not be on a lead and may be as shown above, for example, in FIG. 17A-17B, 18A-18B, 19A-19C, 20A-20C, or 21A-21C. A stand-alone sensor may be implanted and secured by, for example, the use of anchoring in the mediastinum as described in US PG Patent Application Pub. No. 20170021159, titled SUBSTERNAL PLACEMENT OF A PACING OR DEFIBRILLATING ELECTRODE, the disclosure of which is incorporated herein by reference. Such anchoring may be achieved by the use of an elongated anchor placement tool for placing an anchor in the connective tissue in the region of the sternal angle and/or the $2^{nd}$ or $3^{rd}$ rib, and/or superior to the ventricles, and/or inferior to or at the manubrium, and/or approximately level with the thymus, superior vena cava, or aortic arch. An implanted sensor may be provided with a suture hole to allow anchoring by the use of a tether. For example, the anchor itself may be implanted as described in the Ser. No. 15/208,682 application with a tether attached thereto, and the sensor can be attached at one end of the tether while the other end of the tether is pulled to draw the sensor into the mediastinum. Anchoring using a tether and anchor as described in the Ser. No. 15/208,682 application may omit passing through the ITV and may instead be performed by accessing the mediastinum from a position inferior to the lower rib margin and passing an anchor placement tool along the back side of the sternum until a desire anchor position is reached.

In the above description, the terms inferior and superior are meant to convey anatomical position, and not desirability or greater or lesser functional value.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of treating a patient comprising:
implanting a first electrode in the patient in at least one of the internal thoracic veins;
implanting a second electrode in the patient in at least one of the azygos, hemiazygos, or accessory hemiazygos veins; and
coupling the first electrode and second electrode to operational circuitry of an implantable cardiac monitoring or stimulus system.

2. The method of claim 1 wherein:
the step of implanting the first electrode comprises passing the first electrode through the brachiocephalic vein and to the at least one of the internal thoracic veins; and
the step of implanting the second electrode comprises passing the second electrode through the brachiocephalic vein and then into the azygos vein.

3. The method of claim 1 wherein the step of implanting the first electrode comprises directly accessing the internal thoracic vein at a parasternal location between two ribs, and passing the first electrode through the parasternal location.

4. The method of claim 1 wherein the step of implanting the first electrode comprises accessing a superior epigastric vein or musculophrenic vein of the patient at a location inferior to or at the lower rib margin and then accessing the internal thoracic vein by advancing the first electrode superiorly therefrom.

5. The method of claim 1 wherein the step of implanting the first electrode comprises accessing an intercostal vein, advancing the first electrode therethrough to the internal thoracic vein.

6. The method of claim 1 wherein the step of implanting the second electrode is performed by accessing an intercostal vein and passing the second electrode therethrough to one of the azygos, hemiazygos, or accessory hemiazygos veins.

7. The method of claim 1 wherein the first and second electrodes are disposed on respective first and second leads.

8. The method of claim 7 wherein the step of coupling the first electrode and second electrode to operational circuitry of an implantable cardiac monitoring or stimulus system is performed by coupling the respective first and second leads to a canister of an implantable cardiac stimulus system, and the method further comprises implanting the canister in a subcutaneous location.

9. The method of claim 8 wherein the step of implanting the canister in a subcutaneous location is performed by placing the canister in the left axilla of the patient.

10. The method of claim 9 wherein the first and second leads are implanted such that each will enter and pass through one or more intercostal veins.

11. The method of claim 8 wherein the step of implanting the canister in a subcutaneous location is performed by placing the canister near the clavicle of the patient.

12. The method of claim 11 wherein the first and second leads are implanted such that each will enter and pass through at least a portion of a brachiocephalic vein.

* * * * *